United States Patent [19]

Kerrigan et al.

[11] Patent Number: 5,767,116

[45] Date of Patent: Jun. 16, 1998

[54] BICYCLIC AROMATIC COMPOUNDS AS THERAPEUTIC AGENTS

[75] Inventors: Frank Kerrigan; David John Heal; Keith Frank Martin, all of Nottingham, United Kingdom

[73] Assignee: Knoll Atkiengesellschaft, Ludwigshafen, Germany

[21] Appl. No.: 605,130

[22] PCT Filed: Sep. 1, 1994

[86] PCT No.: PCT/EP94/02904

§ 371 Date: Jun. 5, 1996

§ 102(e) Date: Jun. 5, 1996

[87] PCT Pub. No.: WO95/07274

PCT Pub. Date: Mar. 16, 1995

[30] Foreign Application Priority Data

Sep. 6, 1993 [GB] United Kingdom ............. 9318431

[51] Int. Cl.$^6$ .............. A61K 31/445; A61K 31/505; C07D 403/14; C07D 401/14

[52] U.S. Cl. .............. 514/212; 514/253; 514/259; 514/256; 514/318; 514/321; 514/422; 548/526; 546/194; 546/197; 540/596; 544/283; 544/405

[58] Field of Search .............. 544/284, 283, 544/405; 540/596; 546/194, 197; 548/526; 514/212, 253, 259, 256, 318, 321, 422

[56] References Cited

U.S. PATENT DOCUMENTS

| | | | |
|---|---|---|---|
| 4,569,933 | 2/1986 | Cornu et al. | 514/237 |
| 4,749,702 | 6/1988 | Janssens et al. | 514/253 |
| 5,137,901 | 8/1992 | Junge et al. | 514/373 |
| 5,182,292 | 1/1993 | Stack | 514/321 |
| 5,192,775 | 3/1993 | Malen et al. | 514/321 |
| 5,286,735 | 2/1994 | Bonnaud et al. | 514/321 |

FOREIGN PATENT DOCUMENTS

| | | |
|---|---|---|
| 054 304 | 6/1982 | European Pat. Off. . |
| 054304 | 6/1982 | European Pat. Off. . |
| 184257 | 6/1986 | European Pat. Off. ...... C07D 413/12 |
| 445 026 | 9/1991 | European Pat. Off. . |
| 58154574 | 9/1983 | Japan . |
| 93/17017 | 9/1993 | WIPO . |

OTHER PUBLICATIONS

Klein et al., Journal of Pharmaceutical Sciences, vol. 74, No. 11, Nov., 1985, pp. 1147–1151.

Fifer et al., European Journal of Medicinal Chemistry, vol. 19, No. 6, 1984, pp. 519–524.

Jacobsen, National Institute on Drug Abuse Research Monograph Series, 1992, pp. 437–458, 1993.

Mitsubishi Chem., Chemical Abstract, vol. 100, No. 28, 1984, Abstracts No. 100:103,366m.

Chem. Abst., vol. 100, No. 28, 1984, abst. 103366m, p. 655.

Primary Examiner—Matthew V. Grumbling
Attorney, Agent, or Firm—Keil & Weinkauf

[57] ABSTRACT

Compounds of formula I

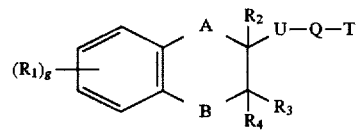

and pharmaceutically acceptable salts thereof in which A is methylene or —O—; B is methylene or —O—; and g is 0, 1, 2, 3 or 4;

$R_1$, $R_2$, $R_3$, $R_4$, U, Q and T are defined in claim 1.

The compounds have utility in the treatment of central nervous system disorders, for example depression, anxiety, psychoses (for example schizophrenia), tardive dyskinesia, Parkinson's disease, obesity, hypertension, Tourette's syndrome, sexual dysfunction, drug addiction, drug abuse, cognitive disorders, Alzheimer's disease, senile dementia, obsessive-compulsive behaviour, panic attacks, eating disorders and anorexia, cardiovascular and cerebrovascular disorders, non-insulin dependent diabetes mellitus, hyperglycaemia, constipation, arrhythmia, disorders of the neuroendocrine system, stress, prostatic hypertrophy, and spasticity.

10 Claims, No Drawings

BICYCLIC AROMATIC COMPOUNDS AS THERAPEUTIC AGENTS

This is a national stage application filed under 35U.S.C. 0371 of PCT/EP94/02904, filed Sep. 1, 1994.

The present invention relates to novel therapeutic agents which have affinity for 5-HT$_{1A}$ and/or $\alpha_1$ and/or $\alpha_2$ and/or D$_2$ receptors, to processes for their preparation, to pharmaceutical compositions containing them and to their use in the treatment of central nervous system disorders, for example depression, anxiety, psychoses (for example schizophrenia), tardive dyskinesia, Parkinson's disease, obesity, hypertension, Tourette's syndrome, sexual dysfunction, drug addiction, drug abuse, cognitive disorders, Alzheimer's disease, senile dementia, obsessive-compulsive behaviour, panic attacks, eating disorders and anorexia, cardiovascular and cerebrovascular disorders, non-insulin dependent diabetes mellitus, hyperglycaemia, constipation, arrhythmia, disorders of the neuroendocrine system, stress, prostatic hypertrophy, and spasticity.

In WO93/17017 there are described [(benzodioxanyl, benzofuranyl and benzopyranyl)alkylamino]alkyl substituted 2-pyrimidinyl compounds which have vasoconstrictor activity. These compounds are claimed to be useful in treating conditions related to vasodilation.

The present invention provides compounds of formula I

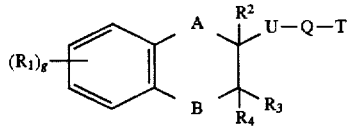

including pharmaceutically acceptable salts thereof in which

A is methylene or —O—;

B is methylene or —O—;

g is 0,1,2,3 or 4;

R$_1$ represents a) halo, b) an alkyl group containing 1 to 3 carbon atoms optionally substituted by one or more halo, c) an alkoxy group containing 1 to 3 carbon atoms optionally substituted by one or more halo, d) an alkylthio group containing 1 to 3 carbon atoms optionally substituted by one or more halo, e) hydroxy, f) an acyloxy group containing 1 to 3 carbon atoms, g) hydroxymethyl, h) cyano, i) an alkanoyl group containing 1 to 6 carbon atoms, j) an alkoxycarbonyl group containing 2 to 6 carbon atoms, k) a carbamoyl group or carbamoylmethyl group each optionally N-substituted by one or two alkyl groups each containing 1 to 3 carbon atoms, l) a sulphamoyl or sulphamoylmethyl group each optionally N-substituted by one or two alkyl groups each containing 1 to 3 carbon atoms, m) an amino group optionally substituted by one or two alkyl groups each containing 1 to 3 carbon atoms; or two adjacent R$_1$ groups together with the carbon atoms to which they are attached form a fused benz ring, the substituents represented by R$_1$ being the same or different when g is 2,3 or 4;

R$_2$ is H, an alkyl group containing 1 to 3 carbon atoms, or an alkoxy group containing 1 to 3 carbon atoms;

R$_3$ and R$_4$, which are the same or different, are H, or an alkyl group containing 1 to 3 carbon atoms;

U is an alkylene chain containing 1 to 3 carbon atoms, optionally substituted by one or more alkyl groups each containing 1 to 3 carbon atoms;

Q represents a divalent group of formula IIa, IIb or IIc

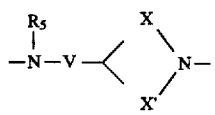

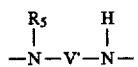

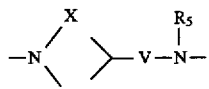

in which V is a bond or an alkylene chain containing 1 to 3 carbon atoms optionally substituted by one or more alkyl groups each containing 1 to 3 carbon atoms;

V' is an alkylene chain containing 2 to 6 carbon atoms, optionally substituted by one or more alkyl groups each containing 1 to 3 carbon atoms;

X is an alkylene chain containing 0 to 2 carbon atoms and X' is an alkylene chain containing 1 to 4 carbon atoms provided that the total number of carbon atoms in X and X' amounts to 3 or 4; R$_5$ is H or an alkyl group containing 1 to 3 carbon atoms; and T represents an aromatic group optionally containing one or more N atoms and optionally substituted by one or more substituents selected from halo, an alkyl group containing 1 to 3 carbon atoms, an alkoxy group containing 1 to 3 carbon atoms, or a polyhalogenated alkyl group, for example trifluoromethyl, or T represents benzo[b]furanyl or benzodioxanyl with the proviso that T is not 2-pyrimidinyl when A is —O—.

In preferred compounds of formula I, A is —O—.

In preferred compounds of formula I, B is —O—.

In more preferred compounds of formula I both A and B are —O—.

In preferred compounds of formula I, g is 0,1 or 2.

In preferred compounds of formula I, R$_1$ represents halo (for example fluoro, chloro, or bromo), an alkyl group containing 1 to 3 carbon atoms, an alkoxy group containing 1 to 3 carbon atoms, hydroxy, or two adjacent R$_1$ groups together with the carbon atoms to which they are attached form a fused benz ring. In more preferred compounds of formula I, R$_1$ represents methoxy, fluoro, chloro, hydroxy, or two adjacent R$_1$ groups together with the carbon atoms to which they are attached form a fused benz ring.

In preferred compounds of formula I, R$_2$ is H or an alkyl group containing 1 to 3 carbon atoms. In more preferred compounds of formula I, R$_2$ is H.

In preferred compounds of formula I, R$_3$ and R$_4$, which are the same or different, are H or methyl. In more preferred compounds of formula I, R$_3$ and R$_4$ are both H.

In preferred compounds of formula I, U is methylene.

In preferred compounds of formula I in which Q is a group of formula IIa or IIc, V is methylene or ethylene.

In preferred compounds of formula I, in which Q is a group of formula IIb, V' is an alkylene chain containing 2 to 4 carbon atoms.

In preferred compounds of formula I, R$_5$ is H or methyl. In more preferred compounds of formula I, R$_5$ is H.

In preferred compounds of formula I, T is pyridyl, pyrimidinyl, pyrazinyl, phenyl, benzo[b]furanyl, 1,4-benzodioxanyl or quinazolinyl all optionally substituted by methoxy, trifluoromethyl, or halo (eg fluoro, chloro or bromo). In more preferred compounds of formula I, T is 2-pyridyl, 2-pyrimidinyl, 2-pyrazinyl, phenyl, 2,3- dihydrobenzo[b]furan-7-yl, 1,4-benzodioxan-5-yl or 4-quinazolinyl all optionally substituted by methoxy, trifluoromethyl, or halo (eg fluoro, chloro or bromo).

Compounds of formula I may exist as salts with pharmaceutically acceptable acids. Examples of such salts include hydrochlorides, hydrobromides, sulphates, methanesulphonates, nitrates, maleates, acetates, citrates, fumarates, tartrates [eg (+)-tartrates, (−)-tartrates or mixtures thereof including racemic mixtures], succinates, benzoates and salts with amino acids such as glutamic acid. Compounds of formula I and their salts may exist in the form of solvates (for example hydrates).

Compounds of formula I contain one or more chiral centres, and exist in different optically active forms. When compounds of formula I contain one chiral centre, the compounds exist in two enantiomeric forms and the present invention includes both enantiomers and mixtures of enantiomers. The enantiomers may be resolved by methods known to those skilled in the art, for example by formation of diastereoisomeric salts which may be separated, for example, by crystallisation; formation of diastereoisomeric derivatives or complexes which may be separated, for example, by crystallisation, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesised by asymmetric synthesis using optically active reagents, substrates, catalysts or solvents, or by converting one enantiomer into the other by asymmetric transformation.

When a compound of formula I contains more than one chiral centre it may exist in diastereoisomeric forms. The diastereoisomeric pairs may be separated by methods known to this skilled in the art, for example chromatography or crystallisation and the individual enantiomers within each pair may be separated as described above. The present invention includes each diastereoisomer of compounds of formula I and mixtures thereof.

Certain compounds of formula I and their salts may exist in more than one crystal form and the present invention includes each crystal form and mixtures thereof. Certain compounds of formula I and their salts may also exist in the form of solvates, for example hydrates, and the present invention includes each solvate and mixtures thereof.

Specific compounds of formula I are:
N-(1,4-Benzodioxan-2-ylmethyl)-1-[1-(pyrazin-2-yl)piperid-4-yl]methylamine;
N-(1,4-Benzodioxan-2-ylmethyl)-1-[1-(2-methoxyphenyl)piperid-4-yl]methylamine;
N-(1,4-Benzodioxan-2-ylmethyl)-1-[1-(3-chloropyrid-2-yl)piperid-4-yl]methylamine;
N-(1,4-Benzodioxan-2-ylmethyl)-1-[1-(quinazolin-4-yl)piperid-4-yl]methylamine;
N-(1,4-Benzodioxan-2-ylmethyl)-1-[1-(pyrid-2-yl)piperid-4-yl]methylamine;
N-(8-Methoxy-1,4-benzodioxan-2-ylmethyl)-1-[1-(2-methoxyphenyl)piperid-4-yl]methylamine;
N-(1,4-Benzodioxan-2-ylmethyl)-N'-[3-(trifluoromethyl)-2-pyridyl]ethanediamine;
N-(8-Methoxy-1,2,3,4-tetrahydronaphth-2-ylmethyl)-1-[1-pyrimidin-2-yl)piperid-4-yl]methylamine;
7-{N-[1-(Pyrimidin-2-yl)piperid-4-ylmethyl]aminomethyl}-5,6,7,8-tetrahydronaphth-1-ol;
N-(5-Methoxy-3,4-dihydro-2H-1-benzopyran-3-ylmethyl)-1-[1-(pyrimidin-2-yl)piperid-4-yl]methylamine;
N-(1,4-Benzodioxan-2-ylmethyl)-1-(1-phenylpiperid-4-yl)methylamine;
N-(1,4-Benzodioxan-2-ylmethyl)-1-[1-(1,4-benzodioxan-5-yl)piperid-4-yl]methylamine;
1-[1-(1,4-Benzodioxan-2-ylmethyl)piperid-4-yl]-N-(2-methoxyphenyl)methylamine;
N-(1,4-Benzodioxan-2-ylmethyl)-1-[1-(4-methoxyphenyl)piperid-4-yl]methylamine;
N-(8-Methoxy-1,4-benzodioxan-2-ylmethyl)-N'-(2-methoxyphenyl)-1,3-propanediamine;
N-(1,4-Benzodioxan-2-ylmethyl)-1-[1-(3-methoxyphenyl)piperid-4-yl]methylamine;
N-(6,7-Dichloro-1,4-benzodioxan-2-ylmethyl)-1-[1-(2-methoxyphenyl)piperid-4-yl]methylamine;
N-(1,4-Benzodioxan-2-ylmethyl)-1-[1-(2-chlorophenyl)piperid-4-yl]methylamine;
N-(5-Fluoro-1,4-benzodioxan-2-ylmethyl)-1-[1-(2-methoxyphenyl)piperid-4-yl]methylamine;
N-(8-Fluoro-1,4-benzodioxan-2-ylmethyl)-1-[1-(2-methoxyphenyl)piperid-4-yl]methylamine;
1-[1-(2-methoxyphenyl)piperid-4-yl]-N-(naphtho[1,2-b]dioxan-2-ylmethyl)methylamine;
1-[1-(2,3-Dihydrobenzo[b]furan-7-yl)piperid-4-yl]-N-(8-methoxy-1,4-benzodioxan-2-ylmethyl)methylamine;
N-(6-chloro-1,4-benzodioxan-2-ylmethyl)-1-[1-(2-methoxyphenyl)piperid-4-yl]methylamine;
N-(7-chloro-1,4-benzodioxan-2-ylmethyl)-1-[1-(2-methoxyphenyl)piperid-4-yl]methylamine;
N-(8-hydroxy-1,4-benzodioxan-2-ylmethyl)-1-[1-(2-methoxyphenyl)piperid-4-yl]methylamine;
and pharmaceutically acceptable salts thereof in the form of individual enantiomers, racemates, or other mixtures of enantiomers.

Specific enantiomeric forms of compounds of formula I include:
(S)-(−)-N-(1,4-Benzodioxan-2-ylmethyl)-1-[1-(2-methoxyphenyl)piperid-4-yl]methylamine;
(R)-(+)-N-(1,4-Benzodioxan-2-ylmethyl)-1-[1-(2-methoxyphenyl)piperid-4-yl]methylamine;
(−)-N-(1,4-Benzodioxan-2-ylmethyl)-1-[1-(pyrid-2-yl)piperid-4-yl]methylamine dihydrochloride;
(+)-N-(1,4-Benzodioxan-2-ylmethyl)-1-[1-(pyrid-2-yl)piperid-4-yl]methylamine dihydrochloride.

The present invention also includes pharmaceutical compositions containing a therapeutically effective amount of a compound of formula I or a salt thereof together with a pharmaceutically acceptable diluent or carrier.

As used hereinafter, the term "active compound" denotes a compound of formula I or a salt thereof. In therapeutic use, the active compound may be administered orally, rectally, parenterally or topically, preferably orally. Thus the therapeutic compositions of the present invention may take the form of any of the known pharmaceutical compositions for oral, rectal, parenteral or topical administration. Pharmaceutically acceptable carriers suitable for use in such compositions are well known in the art of pharmacy. The compositions of the invention may contain 0.1–99% by weight of active compound. The compositions of the invention are generally prepared in unit dosage form. Preferably the unit dosage of active ingredient is 1–500 mg. The excipients used in the preparation of these compositions are the excipients known in the pharmacist's art.

Compositions for oral administration are the preferred compositions of the invention and these are the known pharmaceutical forms for such administration, for example tablets, capsules, syrups and aqueous or oil suspensions. The excipients used in the preparation of these compositions are the excipients known in the pharmacist's art. Tablets may be prepared by mixing the active compound with an inert diluent such as calcium phosphate in the presence of disintegrating agents, for example maize starch, and lubricating agents, for example magnesium stearate, and tableting the mixture by known methods. The tablets may be formulated in a manner known to those skilled in the art so as to give a sustained release of the compounds of the present invention. Such tablets may, if desired, be provided with enteric coatings by known methods, for example by the use of cellulose acetate phthalate. Similarly, capsules, for example hard or soft gelatin capsules, containing the active compound with or without added excipients, may be prepared by conventional means and, if desired, provided with enteric coatings in a known manner. The tablets and capsules may conveniently each contain 1 to 500 mg of the active compound. Other compositions for oral administration include, for example, aqueous suspensions containing the active compound in an aqueous medium in the presence of a non-toxic suspending agent such as sodium carboxymethylcellulose, and oily suspensions containing a compound of the present invention in a suitable vegetable oil, for example arachis oil.

The active compound may be formulated into granules with or without additional excipients. The granules may be ingested directly by the patient or they may be added to a suitable liquid carrier (for example water) before ingestion. The granules may contain disintegrants (for example a pharmaceutically acceptable effervescent couple formed from an acid and a carbonate or bicarbonate salt) to facilitate dispersion in the liquid medium.

Compositions of the invention suitable for rectal administration are the known pharmaceutical forms for such administration, for example, suppositories with cocoa butter or polyethylene glycol bases.

Compositions of the invention suitable for parenteral administration are the known pharmaceutical forms for such administration, for example sterile suspensions or sterile solutions in a suitable solvent.

Compositions for topical administration may comprise a matrix in which the pharmacologically active compounds of the present invention are dispersed so that the compounds are held in contact with the skin in order to administer the compounds transdermally. A suitable transdermal composition may be prepared by mixing the pharmaceutically active compound with a topical vehicle, such as a mineral oil, petrolatum and/or a wax, for example paraffin wax or beeswax, together with a potential transdermal accelerant such as dimethyl sulphoxide or propylene glycol. Alternatively the active compounds may be dispersed in a pharmaceutically acceptable cream or ointment base. The amount of active compound contained in a topical formulation should be such that a therapeutically effective amount of the compound is delivered during the period of time for which the topical formulation is intended to be on the skin.

The compounds of the present invention may also be administered by continuous infusion either from an external source, for example by intravenous infusion or from a source of the compound placed within the body. Internal sources include implanted reservoirs containing the compound to be infused which is continuously released for example by osmosis and implants which may be (a) liquid such as a suspension or solution in a pharmaceutically acceptable oil of the compound to be infused for example in the form of a very sparingly water-soluble derivative such as a dodecanoate salt or ester or (b) solid in the form of an implanted support, for example of a synthetic resin or waxy material, for the compound to be infused. The support may be a single body containing all the compound or a series of several bodies each containing part of the compound to be delivered. The amount of active compound present in an internal source should be such that a therapeutically effective amount of the compound is delivered over a long period of time.

In some formulations it may be beneficial to use the compounds of the present invention in the form of particles of very small size, for example as obtained by fluid energy milling.

In the compositions of the present invention the active compound may, if desired, be associated with other compatible pharmacologically active ingredients.

The pharmaceutical compositions containing a therapeutically effective amount of a compound of formula I or a salt thereof may be used to treat depression, anxiety, psychoses (for example schizophrenia), tardive dyskinesia, Parkinson's disease, obesity, hypertension, Tourette's syndrome, sexual dysfunction, drug addiction, drug abuse, cognitive disorders, Alzheimer's disease, senile dementia, obsessive-compulsive behaviour, panic attacks, eating disorders, anorexia, cardiovascular and cerebrovascular disorders, non-insulin dependent diabetes mellitus, hyperglycaemia, constipation, arrhythmia, disorders of the neuroendocrine system, stress, prostatic hypertrophy, and spasticity in human beings. Whilst the precise amount of active compound administered in such treatment will depend on a number of factors, for example the age of the patient, the severity of the condition and the past medical history and always lies within the sound discretion of the administering physician, the amount of active compound administered per day is in the range 1 to 1000 mg preferably 5 to 500 mg given in single or divided doses at one or more times during the day.

Processes for the preparation of compounds of formula I will now be described. These processes form a further aspect of the present invention.

Compounds of formula I in which Q is a group of formula IIa in which $R_5$ is H, and V is $(CH_2)_{n+1}$ wherein n is 0,1 or 2 may be prepared by the reaction of a compound of formula III

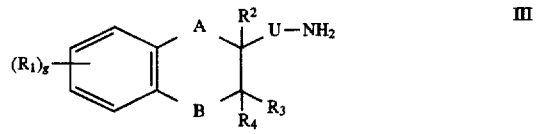

with a compound of formula IV

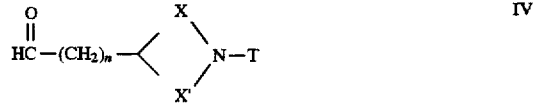

followed by reaction of the intermediate imine with a reducing agent, for example sodium borohydride.

Compounds of formula I in which Q is a group of formula IIa in which $R_5$ is H, and V is $(CH_2)_{n+1}$ wherein n is 0,1 or 2 may be prepared by the reaction of a compound of formula III with a compound of formula V

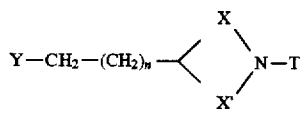

in which Y is a leaving group, for example toluene-4-sulphonyloxy, optionally in the presence of a suitable solvent, optionally in the presence of a base, for example potassium carbonate.

Compounds of formula I in which Q is a group of formula IIa in which $R_5$ is H, and V is $(CH_2)_{n+1}$ wherein n is 0,1 or 2 may be prepared by reaction of a compound of formula VI

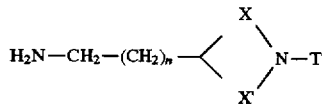

with a compound of formula VII

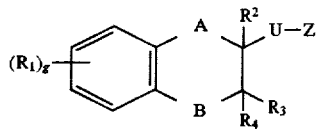

in which Z is a leaving group, for example toluene-4-sulphonyloxy, optionally in the presence of a suitable solvent, optionally in the presence of a base, for example potassium carbonate.

Compounds of formula I in which U is methylene and Q is a group of formula IIa in which $R_5$ is H, and V is $(CH_2)_{n+1}$ wherein n is 0,1 or 2 may be prepared by reaction of a compound of formula VIII

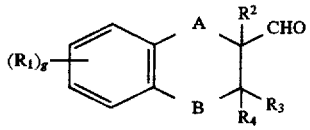

with a compound of formula VI, followed by reduction of the intermediate imine with a suitable reducing agent, for example sodium borohydride.

Compounds of formula I in which $R_5$ is an alkyl group may be prepared by alkylation of a compound of formula I in which $R_5$ is H with for example formaldehyde and formic acid, or an aldehyde and a reducing agent such as sodium cyanoborohydride.

Compounds of formula III, in which U is $(CH_2)_{m+1}$ wherein m is 0,1 or 2 may be prepared by reduction of a compound of formula IX

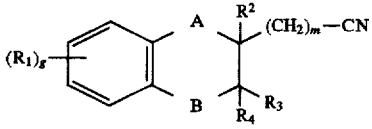

with a reducing agent, for example lithium aluminium hydride.

Compounds of formula IX in which A and B are both O may be prepared by reaction of a compound of formula X

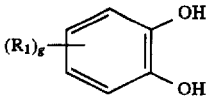

with a vicinally disubstituted nitrile compound of formula XI

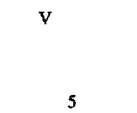 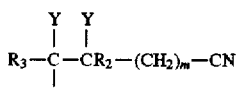

in which Y is a leaving group such as halo, for example bromo, in the presence of a base, for example potassium carbonate.

Compounds of formula III may be prepared from compounds of formula XII

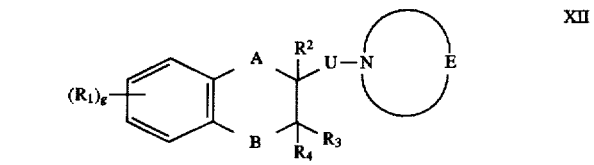

in which E together with the nitrogen atom to which it is attached is a cyclic imide, for example a phthalimide, by acid or base catalysed hydrolysis or by cleavage with a reagent, for example hydrazine hydrate.

Compounds of formula XII in which E together with the nitrogen atom to which it is attached is a phthalimide may be prepared by reaction of a compound of formula VII in which Z is a leaving group, for example toluene-4-sulphonyloxy, with potassium phthalimide.

Compounds of formula III in which U is methylene may be prepared by reduction of a compound of formula XIII

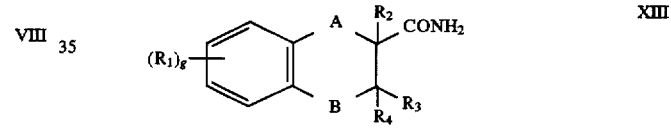

with a suitable reducing agent, for example lithium aluminium hydride.

Compounds of formula XIII may be prepared by reaction of a compound of formula XIV

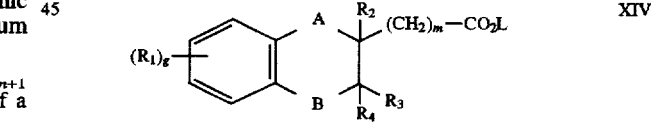

in which m is 0 and L is an alkyl group containing 1 to 6 carbon atoms with ammonia.

Compounds of formula IV may be prepared by reaction of a compound of formula XV

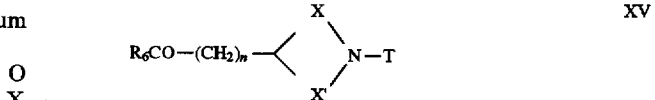

in which $R_6$ is an alkoxy group containing 1 to 4 carbon atoms, with a reducing agent, for example sodium bis (2-methoxyethoxy)aluminium hydride in a solvent, for example toluene.

Compounds of formula XV may be prepared by reaction of a compound of formula XVI

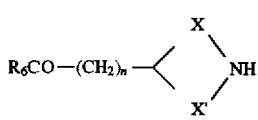

with a haloaromatic compound, for example a 2-halopyridine such as 2-chloropyridine, optionally in the presence of a base, for example triethylamine.

Compounds of formula IV may also be prepared by oxidation of a compound of formula XVII

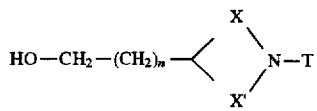

with a suitable oxidising agent, for example oxalyl chloride/ dimethyl sulphoxide.

Compounds of formula V in which Y is toluene-4-sulphonyloxy may be prepared by reaction of a compound of formula XVII with a tosylating agent, for example toluene-4-sulphonyl chloride.

Compounds of formula XVII may be prepared by reduction of a compound of formula XV with a reducing agent, for example lithium aluminium hydride, or by reaction of a compound of formula XVIII

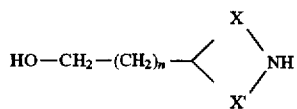

with a haloaromatic compound, for example a 2-halopyridine such as 2-chloropyridine, optionally in the presence of a base, for example triethylamine.

Compounds of formula XVIII may be prepared by reduction of a compound of formula XVI, in which $R_6$ is an alkoxy group containing 1 to 4 carbon atoms, with a reducing agent, for example lithium aluminium hydride.

Compounds of formula VI may be prepared by reaction of a compound of formula XIX

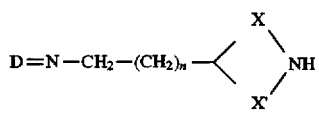

in which D is a protecting group, for example α-methylbenzylidene or 4-nitrobenzylidene with a haloaromatic compound, for example a 2-halopyridine such as 2-chloropyridine, optionally in the presence of a base, for example triethylamine, followed by removal of the protecting group, for example by acid-catalysed hydrolysis.

Compounds of formula XIX may be prepared by reaction of a compound of formula XX

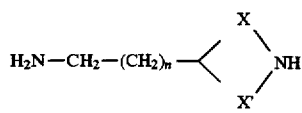

with a protecting reagent, for example acetophenone or 4-nitrobenzaldehyde.

Compounds of formula VI may be prepared directly by reaction of a compound of formula XX with a haloaromatic compound, for example a halopyridine such as 2-chaoropyridine, optionally in the presence of a base, for example potassium carbonate.

Compounds of formula XX may be prepared by reduction of a compound of formula XVI in which $R_6$ is $NH_2$ with a reducing agent, for example lithium aluminium hydride.

Compounds of formula VI may also be prepared by reaction of a compound of formula XXI

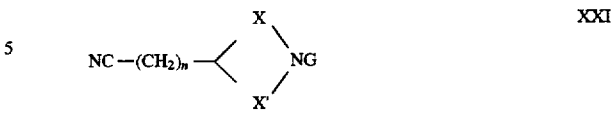

in which G is H with a haloaromatic compound such as 2-chloropyridine optionally in the presence of a base, for example triethylamine, followed by reduction with a reducing agent, for example lithium aluminium hydride.

Compounds of formula XXI in which G is H may be prepared by reaction of a compound of formula XXI in which G is an alkyl or arylalkyl group, for example benzyl, with a dealkylating agent, for example 1-chloroethyl chloroformate, followed by cleavage of the intermediate carbamate.

Compounds of formula XX may also be prepared by reaction of a compound of formula XXI in which G is an amine protecting group, for example benzyl, with a reducing agent, for example lithium aluminium hydride, followed by protecting group removal, for example by reaction with formic acid in the presence of a palladium-on-carbon catalyst.

Compounds of formula VI may be prepared by reduction of a compound of formula XXII

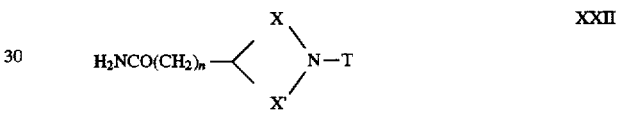

with a reducing agent, for example borane-dimethyl sulphide complex or lithium aluminium hydride.

Compounds of formula XXII in which the total number of carbon atoms in X and X' amounts to 4 and in which T is an aromatic group which does not contain N atoms may be prepared by reduction of a compound of formula XXIII

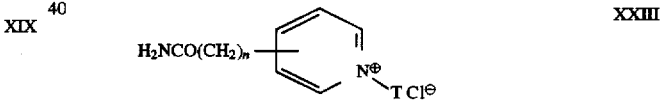

in which T is an aromatic group which does not contain N atoms, with a reducing agent, for example ammonium formate or hydrogen in the presence of a palladium-on-carbon catalyst.

Compounds of formula XXIII may be prepared by displacement of 2,4-dinitroaniline from a compound of formula XXIV

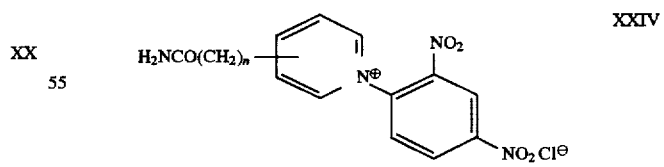

by reaction with a compound of formula XXV

in which T is an aromatic group which does not contain N atoms.

Compounds of formula XXIV may be prepared by reaction of 2,4-dinitrochlorobenzene with a compound of formula XXVI

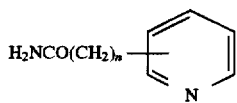

XXVI

Compounds of formula VII in which Z is toluene-4-sulphonyloxy may be prepared by reaction of a compound of formula XXVII

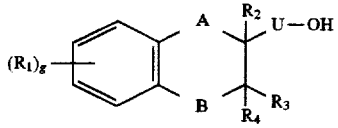

XXVII with toluene-4-sulphonyl chloride, optionally in the presence of a base, for example pyridine.

Compounds of formula XXVII in which U is $(CH_2)_{m+1}$ may be prepared by reduction of a compound of formula XIV in which L is an alkyl group containing 1 to 4 carbon atoms and m is 0, 1 or 2, with a reducing agent, for example lithium aluminium hydride.

Compounds of formula XXVII in which A and B are both —O—, $R_2$, $R_3$ and $R_4$ are all H, and U is methylene may be prepared by reaction of a compound of formula XXVIII

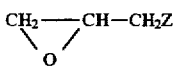

XXVIII in which Z is a leaving group, for example chloro or toluene-4-sulphonyloxy, with a compound of formula X in a suitable solvent, for example water or dimethylformamide in the presence of a base, for example sodium hydroxide. When an enantiomerically pure form of a compound of formula XXVIII, for example (R)-glycidol—O-toluene-4-sulphonate, is used, a single enantiomer of a compound of formula XXVII can be prepared.

Compounds of formula XXVII in which A and B are both —O—, U is methylene, $R_2$, $R_3$ and $R_4$ are all H, and $R_1$ is an alkoxy group containing 1 to 3 carbon atoms may be prepared by alkylation of the corresponding compound of formula XXVII in which $R_1$ is hydroxy by reaction with an alkylating agent, for example methyl iodide, in the presence of a base, for example sodium hydroxide.

Compounds of formula XXVII in which A and B are both —O—, U is methylene, $R_2$ is alkyl and $R_3$ and $R_4$ are H may be prepared by reaction of a compound of formula XXIX

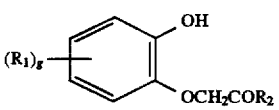

XXIX with a reagent suitable for the conversion of carbonyl compounds into epoxides, for example dimethylsulphoxonium methylide.

Compounds of formula XXIX may be prepared by reaction of a compound of formula X with a halomethyl ketone, for example $ClCH_2COR_2$, in the presence of a base, for example potassium carbonate.

Compounds of formula XXVII in which A and U are methylene, B is —O— and $R_2$ is H, may be prepared by reduction of a compound of formula XXX

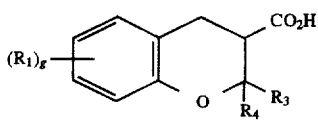

XXX with a reducing agent, for example borane-dimethyl sulphide complex.

Compounds of formula XXX may be prepared by reduction of a compound of formula XXXI

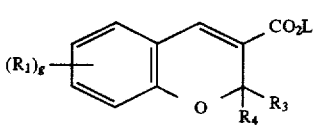

XXXI in which L is H with a reducing agent, for example hydrogen in the presence of a palladium-on-carbon catalyst.

Compounds of formula XXXI in which L is H may be prepared by acid or base-catalysed hydrolysis of a compound of formula XXXI in which L is an alkyl group containing 1 to 6 carbon atoms.

Compounds of formula XXXI in which L is an alkyl group may be prepared by reaction of a compound of formula XXXII

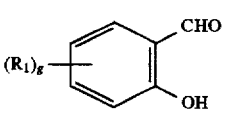

XXXII with a compound of formula XXXIII

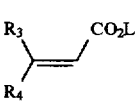

XXXIII in which L is an alkyl group containing 1 to 6 carbon atoms, in the presence of a base, for example 1,4-diazabicyclo[2.2.2]octane (DABCO).

Compounds of formula XXXII may be prepared by reaction of a compound of formula XXXIV

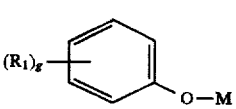

XXXIV in which M is an O-protecting group, for example a 1-ethoxyethyl group, with a metallating agent, for example n-butyllithium, followed by a formylating agent, for example dimethylformamide.

Compounds of formula XXVII in which A, B and U are methylene and $R_2$, $R_3$, and $R_4$ are H may be prepared by reduction of a compound of formula XXXV

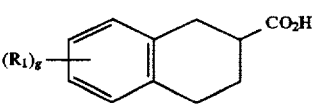

XXXV with a reducing agent, for example borane-dimethyl sulphide complex.

Compounds of formula XXXV may be prepared by Birch reduction of a compound of formula XXXVI

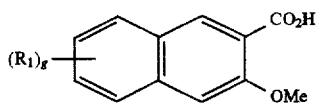

with, for example, lithium in liquid ammonia.

Compounds of formula XXXVI may be prepared by reaction of a compound of formula XXXVII

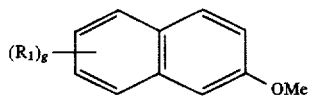

with a metallating agent, for example n-butyllithium, followed by carbon dioxide, followed by acidification of the intermediate carboxylic acid salt.

Compounds of formula VIII may be prepared by oxidation of a compound of formula XXVII in which U is methylene with a suitable oxidising agent, for example pyridinium chlorochromate or by reduction of a compound of formula XIV wherein m is 0 with a suitable reducing agent, for example sodium bis(2-methoxyethoxy)aluminium hydride in a solvent, for example toluene.

Compounds of formula XIV in which A and B are both —O— may be prepared by reaction of a compound of formula XXXVIII

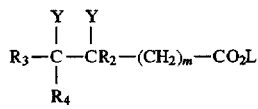

in which Y is a leaving group, for example bromo, and L is an alkyl group containing 1 to 6 carbon atoms with a compound of formula X, in the presence of a base, for example potassium carbonate.

Compounds of formula XIV in which A is methylene, B is —O—, m is 0, $R_2$ is H and L is an alkyl group containing 1 to 6 carbon atoms may be prepared by reduction of a compound of formula XXXI in which L is an alkyl group containing 1 to 6 carbon atoms, with a suitable reducing agent, for example hydrogen in the presence of a palladium-on-carbon catalyst.

Compounds of formula XIV is which A and B are both methylene, m is 0, $R_2$ is H and L is an alkyl group containing 1 to 6 carbon atoms may be prepared by esterification of a compound of formula XXXV with an alcohol of formula LOH, optionally in the presence of an acid or base catalyst.

Compounds of formula I in which Q is a group of formula IIb may be prepared by reaction of a compound of formula XXXIX

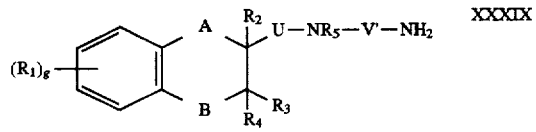

with a haloaromatic compound, for example a 2-halopyridine such as 2-chloropyridine, optionally in the presence of a base, for example, potassium carbonate.

Compounds of formula I in which Q is a group of formula IIb may be prepared by reaction of a compound of formula VII in which Z is a leaving group, for example toluene-4-sulphonyloxy with a compound of formula XL

optionally in the presence of a base, for example potassium carbonate.

Compounds of formula XXXIX may be prepared from a compound of formula XLI

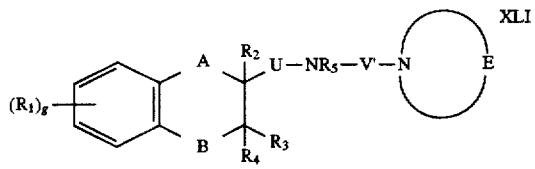

in which E together with the nitrogen atom to which it is attached is a cyclic imide, for example a phthalimide, by acid or base catalysed hydrolysis or by cleavage with a reagent, for example hydrazine hydrate.

Compounds of formula XLI in which E together with the nitrogen atom to which it is attached is a phthalimide and $R_5$ is H may be prepared by reaction of a compound of formula III with a haloalkyl phthalimided for example N-(3-bromopropyl)phthalimide, optionally in the presence of a base, for example potassium carbonate.

Compounds of formula I in which Q is a group of formula IIc may be prepared by reaction of a compound of formula XLII

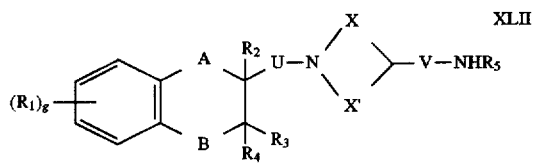

with a haloaromatic compound, for example a 2-halopyridine such as 2-chloropyridine, optionally in the presence of a base, for example triethylamine.

Compounds of formula XLII in which $R_5$ is H may be prepared from compounds of formula XLIII

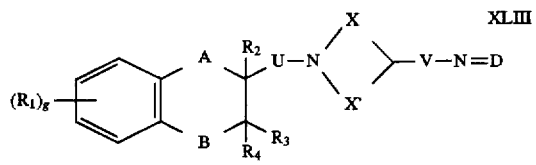

in which D is a protecting group, for example 5-chloro-2-hydroxybenzylidene, by acid or base catalysed hydrolysis.

Compounds of formula XLIII may be prepared by reaction of a compound of formula XLIV

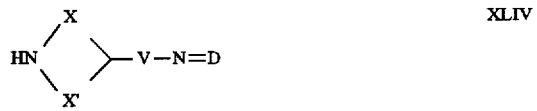

in which D is a protecting group, for example 5-chloro-2-hydroxybenzylidene, with a compound of formula VII, optionally in the presence of a base, for example triethylamine.

Compounds of formula XLIV may be prepared by reaction of a compound of formula XLV

with a protecting reagent, for example 5-chlorosalicylaldehyde.

Compounds of formula I in which Q is a group of formula IIc in which V is $(CH_2)_{n+1}$ wherein n is 0,1 or 2 may also be prepared by the reaction of a compound of formula XLVI

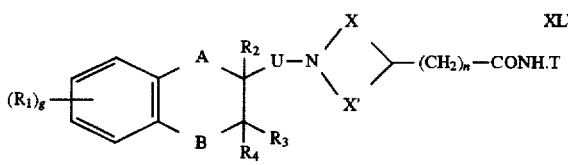

with a reducing agent, for example borane-dimethylsulphide complex.

Compounds of formula XLVI may be prepared by reaction of a compound of formula XLVII

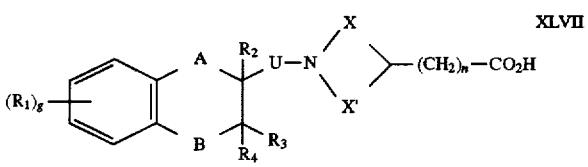

with a mixed anhydride forming agent, for example ethyl chloroformate, optionally in the presence of a base, for example triethylamine, followed by reaction with a compound of formula XXV.

Compounds of formula XLVII may be prepared by hydrolysis of a compound of formula XLVIII

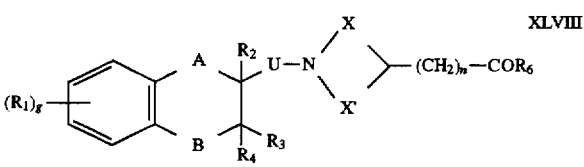

in which $R_6$ is an alkoxy group containing 1 to 4 carbon atoms, with a base, for example potassium hydroxide.

Compounds of formula XLVIII may be prepared by the reaction of a compound of formula VII with a compound of formula XVI in which $R_6$ is an alkoxy group containing 1 to 4 carbon atoms.

The ability of compounds of formula I to interact with 5-hydroxytryptamine (5-HT) receptors has been demonstrated by the following test which determines the ability of the compounds to inhibit tritiated ligand binding to 5-HT receptors in vitro and in particular to $5\text{-HT}_{1A}$ receptors.

Hippocampal tissue from the brains of male Charles River CD rats weighing between 150–250 g were homogenised in ice-cold 50 mM Tris-HCl buffer (pH 7.7) when measured at 25° C., 1:40 w/v) and centrifuged at 30,000 g at 4° C. for 10 minutes. The pellet was rehomogenised in the same buffer, incubated at 37° C. for 10 minutes and centrifuged at 30,000 g at 4° C. for 10 minutes. The final pellet was resuspended in 50 mM Tris-HCl buffer (pH 7.7) containing 4 mM $CaCl_2$, 0.1% L-ascorbic acid and 10 μM pargyline hydrochloride (equivalent to 6.25 mg wet weight of tissue/ml) and used immediately in the binding assay. Aliquots (400 μl; equivalent to 2.5 mg wet weight of tissue/tube) of this suspension were added to tubes containing the ligand (50 μl; 2 nM) and distilled water (50 μl; total binding) or 5-HT (50 μl; 10 gM; non-specific binding) or test compound (50 μl; at a single concentration of $10^{-6}$M or at 10 concentrations ranging from $10^{-11}$–$10^{-3}$M). The ligand was [$^3$H]8-hydroxy-2-(dipropylamino)tetralin([$^3$H]8-OH-DPAT) and the mixture was incubated at 25° C. for 30 minutes before the incubation was terminated by rapid filtration.

The filters were washed with ice-cold Tris-HCl buffer and dried. The filters were punched out into vials, scintillation fluid added and radioactivity determined by liquid scintillation counting. The percentage displacement of specific binding of the tritiated ligand was calculated for the single concentration ($10^{-6}$M) of test compound. Displacement curves were then produced for those compounds which displaced ≧50% of specific binding of the tritiated ligand at $10^{-6}$M using a range of concentrations of the compound. The concentration which gave 50% inhibition of specific binding ($IC_{50}$) was obtained from the curve. The inhibition coefficient Ki was then calculated using the formula $$K_i = \frac{IC50}{1+([\text{ligand}]/K_D)}$$

in which [ligand] is the concentration of the tritiated ligand used and $K_D$ is the equilibrium dissociation constant for the ligand.

The ability of compounds of formula I to interact with adrenoceptor binding sites has been demonstrated by the following test which determines the ability of the compounds to inhibit tritiated ligand binding to adrenoceptors in vitro and in particular $\alpha_1$-adrenoceptors.

Whole cortical tissue from the brains of male Charles River CD rats weighing between 150–250 g were homogenised in ice-cold 50 mM Tris-HCl, pH 7.6 (at 25° C.; 1:40 w/v) and centrifuged at 1000 g at 4° C. for 10 minutes. The supernatant was centrifuged at 30,000 g at 4° C. for 10 minutes. The pellet was rehomogenised in 50 mM Tris-HCl, pH 7.6 (1:40 w/v) and centrifuged at 30,000 g at 4° C. for 10 minutes. The final pellet was resuspended in 50 mM Tris-HCl, pH 7.6 (equivalent to 12.5 mg wet weight of tissue/ml) and used immediately in the binding assay. Aliquots (400 μl; equivalent to 5 mg wet weight of tissue/tube) of this suspension were added to tubes containing the ligand (50 μl; 0.1 nM) and distilled water (50 μl; total binding) or phentolamine (50 μl; 5 μM; non-specific binding) or test compound (50 μl; at a single concentration of $10^{-6}$M or at 10 concentrations ranging from $10^{-11}$–$10^{-3}$M). The ligand was [7-methoxy-$^3$H]prazosin and the mixture was incubated at 30° C. for 30 minutes before the incubation was terminated by rapid filtration.

The filters were washed with ice-cold Tris-HCl buffer and dried. The filters were punched out into vials, scintillation fluid added and radioactivity determined by liquid scintillation counting. The percentage displacement of specific binding of the tritiated ligand was calculated for the single concentration ($10^{-6}$M) of test compound. Displacement curves were then produced for those compounds which displaced ≧50% of specific binding of the tritiated ligand at $10^{-6}$M using a range of concentrations of the compound. The concentration which gave 50% inhibition of specific binding ($IC_{50}$) was obtained from the curve. The inhibition coefficient Ki was then calculated using the formula $$K_i = \frac{IC50}{1+([\text{ligand}]/K_D)}$$

in which [ligand] is the concentration of the tritiated ligand used and $K_D$ is the equilibrium dissociation constant for the ligand.

The ability of compounds of formula I to interact with adrenoceptor binding sites has been demonstrated by the following test which determines the ability of the compounds to inhibit tritiated ligand binding to adrenoceptors in vitro and in particular to the $\alpha_2$-adrenoceptors.

Frontal cortical tissue from the brains of male Charles River CD rats weighing between 150–250 g were homogenised in ice-cold 0.25M sucrose (1:30 w/v) and centrifuged at 1,000 g at 4° C. for 12 minutes. The supernatant was stored on ice and the pellet was rehomogenised in 0.25M sucrose (1:15 w/v) and centrifuged at 850 g at 4° C. for 12 minutes. Combined supernatants were diluted with 5 mM Tris-HCl (pH 7.5) containing 0.5M ethylenediamine tetraacetic acid (EDTA) readjusted to pH 7.5 (at 25° C.) with 1M sodium hydroxide to 1:80 w/v, and centrifuged at 30,000 g at 4° C. for 10 minutes. The resulting pellet was resuspended in 5 mM Tris-HCl (pH 7.5) containing 5.68 mM L-ascorbic acid and 5 mM EDTA readjusted to pH 7.5 (at 25° C.) with 1M sodium hydroxide, and centrifuged at 30,000 g for 10 minutes. The final pellet was resuspended in 50 mM Tris-HCl (pH 7.5) containing 5.68 mM L-ascorbic acid and 5 mM EDTA (equivalent to 12.5 mg wet weight of tissue/ml) and used immediately in the binding assay. Aliquots (400 µl; equivalent to 5 mg wet weight of tissue/tube) of this suspension were added to tubes containing the ligand (50 µl; 1 nM) and distilled water (50 µl; total binding) or phentolamine (50 µl; 5 µM; non-specific binding) or test compound (50 µl; at a single concentration of $10^{-6}$M or at 10 concentrations ranging from $10^{-11}$–$10^{-3}$M). The ligand was tritiated idazoxan ((1,4-[6,7(n)-$^3$H]benzodioxan-2-yl)-2-imidazoline hydrochloride) and the mixture was incubated at 0° C. for 75 minutes before the incubation was terminated by rapid filtration.

The filters were washed with ice-cold Tris-HCl buffer and dried. The filters were punched out into vials, scintillation fluid added and radioactivity determined by liquid scintillation counting. The percentage displacement of specific binding of the tritiated ligand was calculated for the single concentration ($10^{-6}$M) of test compound. Displacement curves were then produced for those compounds which displaced $\geq 50\%$ of specific binding of the tritiated ligand at $10^{-6}$M using a range of concentrations of the compound. The concentration which gave 50% inhibition of specific binding ($IC_{50}$) was obtained from the curve. The inhibition coefficient Ki was then calculated using the formula $$K_i = \frac{IC50}{1 + ([\text{ligand}]/K_D)}$$

in which [ligand] is the concentration of the tritiated ligand used and $K_D$ is the equilibrium dissociation constant for the ligand.

The ability of compounds of formula I to interact with dopamine receptors has been demonstrated by the following test which determines the ability of the compounds to inhibit tritiated ligand binding to dopamine receptors in vitro and in particular to the D2 dopamine receptors.

Striatal tissue from the brains of male Charles River CD rats weighing between 140–250g were homogenised in ice-cold 50 mM Tris-HCl buffer (pH 7.7 when measured at 25° C.) and centrifuged at 40,000 g for 10 minutes. The pellet was resuspended in Tris salts buffer (50 mM Tris-HCl buffer containing 120 mM NaCl, 5 mM KCl, 2 mM CaCl$_2$ and 1 mM MgCl$_2$ with the addition of 6 mM ascorbic acid; pH 7.7 when measured at 25° C.), and again centrifuged at 40,000 g for 10 minutes. The final pellet was stored at –80° C. Before each test the pellet was resuspended in Tris salts buffer (equivalent to 2 mg wet weight of tissue/ml). Aliquots (720 µl; equivalent to 1.44 mg wet weight of tissue/tube) of this suspension were then added to tubes containing the ligand (40 µl; 1 nM) and Tris salts buffer (40 µl; total binding) or spiroperidol (40 µl; 10 nM; non-specific binding) or test compound (40 µl; at a single concentration of $10^{-6}$M or at 6 concentrations ranging from $10^{-11}$–$10^{-4}$M). The ligand was tritiated (S)-sulpiride and the mixture was incubated at 4° C. for 40 minutes before the incubation was terminated by rapid filtration.

The filters were washed with ice-cold Tris-HCl buffer and dried. The filters were punched out in to vials, scintillation fluid added and were left for about 20 hours before being counted by scintillation spectrophotometry. The percentage displacement of specific binding of the tritiated ligand was calculated for the single concentration ($10^{-6}$M) of test compound. Displacement curves were then produced over a range of concentrations for those compounds which displaced $\geq 50\%$ of specific binding of the tritiated ligand at $10^{-6}$M. The concentration which gave a 50% inhibition of specific binding (IC50) was obtained from the curve. The inhibition coefficient Ki was then calculated using the formula $$K_i = \frac{IC50}{1 + ([\text{ligand}]/K_D)}$$

in which [ligand] is the concentration of the tritiated ligand used and $K_D$ is the equilibrium dissociation constant for the ligand.

The Ki values obtained in the above tests for 5-HT$_{1A}$, $\alpha_1$, $\alpha_2$ and D$_2$ binding for each of the final products of Examples 1 to 32 hereinafter are given in Table I below. In some cases it was not possible to determine or estimate the $K_i$ and the $K_i$ value is given as greater than (>) that which would result from the application of the above formula to the highest concentration which displaced $\leq 50\%$ of the ligand.

TABLE 1

| Example Number | Ki (nM) value for | | | |
|---|---|---|---|---|
| | 5-HT$_{1A}$ | $\alpha_2$ | D$_2$ | $\alpha_1$ |
| 1 | 14 | 31 | 15.6 | 23.9 |
| 2 | 7.7 | 394 | 19 | 78 |
| 3 | 1.9 | 86 | 45.3 | 38 |
| 4 | 3.8 | 30 | 35.8 | 13 |
| 5 | 22.6 | 50 | 29 | 79 |
| 6 | 252 | 92% | 8.5 | 3.7 |
| 7 | 96% | 72% | 26.1 | 94% |
| 8 | 18.8 | 70 | 110 | 14 |
| 9 | 8.2 | >500 | 46.4 | 34 |
| 10 | 7.7 | >500 | 310 | 339 |
| 11 | 14.7 | >500 | 12.9 | 31 |
| 12 | 97% | 66% | 39.2 | 89% |
| 13 | 100% | 66% | 22.6 | 93% |
| 14 | 87% | >500 | 63.9 | 57% |
| 15 | 97% | 94% | 68.7 | 94% |
| 16 | 98% | 64% | 35.6 | 94% |
| 17 | 99% | >500 | 4.3 | 93% |
| 18 | 7 | 242 | 53.9 | 35 |
| 19 | 98% | 96% | 23.9 | 98% |
| 20 | 82% | 91% | 26.6 | 94% |
| 21 | 74% | >500 | 104% | >500 |
| 22 | 95% | 63% | 43.5 | 71% |
| 23 | 92% | 75% | 43.0 | 92% |
| 24 | 97% | >500 | 81.3 | >500 |
| 25 | 101% | 96% | 20.9 | 99% |
| 26 | 88% | >500 | 82.5 | >500 |
| 27 | 94% | >500 | 61.7 | 58% |
| 28 | 94% | >500 | 25.1 | >500 |

The % figures in Table 1 are for % displacement at $10^{-6}$M.

The invention is illustrated by the following Examples which are given by way of example only. The final product of each of these Examples was characterised by one or more of the following procedures: gas-liquid chromatography; high performance liquid chromatography; elemental analysis, nuclear magnetic resonance spectroscopy and infrared spectroscopy.

EXAMPLE 1

A mixture of chloropyrazine (14.3 g), 1-(piperid-4-yl) methylamine (14.25 g), sodium carbonate (11.4 g) and 3-methyl-1-butanol (100 ml) was stirred and heated under reflux for 64 hours, cooled to ambient temperature and filtered. The solvent was removed in vacuo and the residual oil was distilled to give 1-[1-(pyrazin-2-yl)piperid-4-yl]methylamine as a pale yellow oil (16.2 g), b.p. 136°–160° C. at 0.6 mbar.

A solution of toluene-4-sulphonyl chloride (60.25 g) in pyridine (75 ml) was added dropwise at 20° C. to a stirred solution of 1-(1,4-benzodioxan-2-yl)methanol (50 g) in pyridine (100 ml) and the mixture was stirred at ambient temperature for 18 hours then poured onto an excess of ice and hydrochloric acid (5M). The resulting solid was collected by filtration, washed well with water and dried in vacuo to give 1,4-benzodioxan-2-ylmethyl toluene-4-sulphonate as an off-white solid (82.3 g), m.p. 75°–78° C.

A mixture of the solid (6.4 g), 1-[1-(pyrazin-2-yl)piperid-4-yl]methylamine (3.8 g), potassium carbonate (50 g), potassium iodide (0.05 g) and acetonitrile (50 ml) was stirred and heated under reflux for 70 hours, then cooled to ambient temperature and filtered. The solid was washed with a little methanol and the filtrate and washings were combined. The solvents were removed in vacuo to leave an oil. The oil was triturated with ether and the solution filtered. The solvent was removed in vacuo to leave an oil (6.2 g) which was purified by Kügelrohr distillation to give an oil (4 g) b.p. ~220° C. at 0.13 mbar. The oil was dissolved in methanol and the solution saturated with hydrogen chloride. The solvent was removed in vacuo to leave a gum which was dissolved in hot ethanol (25 ml) and cooled in ice to give a yellow solid (4 g) which was collected by filtration and dried in vacuo. The solid was dissolved in water and the solution was washed with ethyl acetate and basified by the addition of aqueous sodium hydroxide solution (5M). The free base was extracted into ethyl acetate and the extracts were dried over magnesium sulphate. The solvent was removed in vacuo to leave an oil (2.55 g) which was purified by reduced pressure flash chromatography over silica using a 9:1 mixture of ether and methanol as eluant. Appropriate fractions were combined and the solvent removed in vacuo to leave a colourless oil (2 g). The oil was dissolved in ethanol (50 ml) and the solution was saturated with hydrogen chloride to give a solid which was collected by filtration and dried in vacuo at 80° C. to give N-(1,4-benzodioxan-2-ylmethyl)-1-[1-(pyrazin-2-yl)piperid-4-yl]methylamine 1.4 hydrochloride as a yellow solid (1.4 g), m.p. 242°–245° C.

EXAMPLE 2

A mixture of pyridine-4-carboxamide (8 g) and 2,4-dinitrochlorobenzene (40 g) was heated at 95° C. for 1 hour, cooled, and slurried in a mixture of methanol (60 ml) and ether (600 ml). The supernatant liquid was removed by decantation, and the solid residue slurried in the same solvent mixture twice more.

The solid residue was then boiled with methanol (100 ml), allowed to cool, and the product was collected by filtration and dried in vacuo to give 4-carbamoyl-1-(2,4-dinitrophenyl)pyridinium chloride as a buff powder (15.35 g), m.p. 236°–238° C. (dec).

A mixture of 4-carbamoyl-1-(2,4-dinitrophenyl)-pyridinium chloride (13.6 g), 2-methoxyaniline (10 ml) and methanol (500 ml) was stirred at ambient temperature for 16 hours and the solvent was removed in vacuo. Ether containing a small amount of acetone was added and the mixture heated under reflux until solidification of the product was complete. The product was collected by filtration to give 4-carbamoyl-1-(2-methoxyphenyl)-pyridinium chloride as a yellow solid (11.5 g), m.p. 229°–230° C. (dec).

A mixture of 4-carbamoyl-1-(2-methoxyphenyl)-pyridinium chloride (10.3 g), 10% palladium-on-carbon catalyst (10 g), ammonium formate (20 g) and methanol (200 ml), was stirred at ambient temperature for 20 minutes, then heated under reflux for 3½ hours. The cooled mixture was filtered and the solvent removed in vacuo to leave a blue-grey solid (8.8 g).

A sample of the blue-grey solid (0.75 g) was stirred with hot water and the resulting solid collected by filtration, dried in vacuo and crystallised from 2-propanol to give a grey solid [A] (0.13 g), m.p. 176°–180° C.

The remainder of the blue-grey solid (8.05 g) was suspended in water and the product extracted into ethyl acetate (5×100 ml). The extracts were washed with water, dried over magnesium sulphate and the solvent removed in vacuo to leave a light brown solid (5.0 g) m.p. 167°–172° C. which was crystallised from 2-propanol (60 ml) to give a light brown solid [B] (2.5 g), m.p. 176°–180° C.

The crystallisation liquors were evaporated and the residue crystallised from 2-propanol (10 ml) to give a light brown solid [C] (0.5 g), m.p. 176°–180° C.

[A], [B] and [C] were combined to give a total yield of 1-(2-methoxyphenyl)piperidine-4-carboxamide (3.1 g).

Borane-dimethyl sulphide complex (10M solution in dimethyl sulphide; 4 ml) was added dropwise at 15°–20° C. under nitrogen to a stirred solution of 1-(2-methoxyphenyl)piperidine-4-carboxamide (2.6 g) in tetrahydrofuran (25 ml) and the stirred mixture was heated under reflux for 6 hours. The mixture was allowed to stand at ambient temperature for 16 hours, then it was quenched by slow, dropwise addition to an excess of ice and water. The aqueous mixture was acidified by the addition of hydrochloric acid (5M), rebasified by the addition of aqueous sodium hydroxide solution (5M), and the product was extracted into ether. The extracts were washed with water, then the product was extracted into hydrochloric acid (5M; 2×100 ml, plus 50 ml). The acidic extracts were basified by the addition of aqueous sodium hydroxide solution (5M) and the product was extracted into ether. The extracts were dried over magnesium sulphate and the solvent removed in vacuo to leave an oil (1.05 g) which was chromatographed over silica using a 9:1 mixture of ether and methanol as eluant to remove by-products. The silica was then suspended in methanol and the mixture was heated under reflux for 10 minutes, allowed to cool, and filtered. The solvent was removed in vacuo to leave 1-[1-(2-methoxyphenyl)piperid-4-yl]methylamine as an oil (0.65 g).

A mixture of 1-[1-(2-methoxyphenyl)piperid-4-yl]methylamine (0.65 g), 1,4-benzodioxan-2-ylmethyl toluene-4-sulphonate (0.95 g, prepared in a similar manner to that described in Example 1), potassium carbonate (0.8 g), potassium iodide (0.01 g) and acetonitrile (20 ml) was stirred and heated under reflux for 20 hours, then filtered.

The solvent was removed in vacuo to leave an oil (1 g) which was purified by reduced pressure flash chromatography over silica using a 9:1 mixture of ether and methanol as eluant. Appropriate fractions were combined and the solvents removed in vacuo to leave an oil (0.6 g). The oil was dissolved in ether and the solution saturated with hydrogen chloride to give a solid which was collected by filtration and dried in vacuo to give N-(1,4-benzodioxan-2-ylmethyl)-1-[1-(2-methoxyphenyl)piperid-4-yl]methylamine dihydrochloride as a white solid (0.5 g), m.p. 219°–223° C.

EXAMPLE 3

A stirred mixture of 2,3-dichloropyridine (20 g), 1-(piperid-4-yl)methylamine (30 g), sodium carbonate (30 g) and 3-methyl-1-butanol (100 ml) was heated at 95° C. for 16 hours, then cooled to ambient temperature, diluted with ethyl acetate (200 ml), and filtered. The solvents were removed in vacua, and the residual oil distilled to give 1-[1-(3-chloropyrid-2-yl)piperid-4-yl]methylamine as a colourless oil (22.2 g), b.p. 115°–140° C. at 0.13 mbar.

A stirred mixture of the oil (3.5 g), 1,4-benzodioxan-2-ylmethyl toluene-4-sulphonate (5 g, prepared in a similar manner to that described in Example 1), potassium carbonate (10 g) and acetonitrile (50 ml) was heated under reflux for 24 hours, the solvent was removed in vacua, and the residue diluted with ethyl acetate (100 ml). The resulting suspension was filtered, and the solvent removed in vacuo to leave a brown oil (6.6 g) which was purified via flash chromatography over silica using a 9:1 mixture of ether and methanol as eluant. Appropriate fractions were combined, and the solvents removed in vacua to give two crops of product:

1 a pale yellow oil (2.2 g), and 2 a pale yellow oil (2.2 g).

(1) was dissolved in ether (50 ml) and the solution was saturated with hydrogen chloride. The resulting solid was collected by filtration, washed with ether, and dried in vacua at ambient temperature to give a white solid (2.0 g), m.p. 241°–243° C. (shrinks ~220° C.).

(2) was treated similarly to give a white solid (1.9 g), m.p. 250°–252° C. (shrinks ~220° C.).

The two crops of solid were combined and suspended in a mixture of ethanol (20 ml) and ethyl acetate (20 ml). The mixture was heated under reflux for 5 minutes, allowed to cool to ambient temperature, and the solid collected by filtration, washed with ethyl acetate, and dried in vacuo at 60° C. to give N-(1,4-benzodioxan-2-ylmethyl)-1-[1-(3-chloropyrid-2-yl)piperid-4-yl]methylamine 1,4 hydrochloride as a white solid (3 g), m.p. 251°–253° C. (shrinks ~230° C.).

EXAMPLE 4

A solution of 1-(piperid-4-yl)methylamine (2.15 g) in ethanol (20 ml) was added to a solution of 4-chloroquinazoline (3.1 g) and triethylamine (6 ml) in ethanol (50 ml). The mixture was stirred at ambient temperature for 100 minutes, then the product was collected by filtration, washed with a little ethanol and dried in vacuo at 60° C. to give a solid (3 g), m.p. 226°–227° C. The solid was triturated with hot ethyl acetate (100 ml) and the resulting solid collected by filtration and dried in vacuo at 60° C. to give 1-[1-(quinazolin-4-yl)piperid-4-yl]methylamine hydrochloride as a white solid (2.8 g), m.p. 231°–232° C.

A solution of the solid (1.2 g) in water (250 ml) was basified by the addition of aqueous sodium hydroxide solution (5M) and the free base was extracted into ether. The extract was dried over magnesium sulphate and the solvent removed in vacuo to leave an oil (1 g).

A mixture of the oil (1 g), 1,4-benzodioxan-2-ylmethyl toluene-4-sulphonate (1.3 g, prepared in a similar manner to that described in Example 1), potassium carbonate (1.1 g) and acetonitrile (15 ml) was stirred and heated under reflux for 64 hours, then cooled and filtered. The solid residues were washed with ether and the filtrate and washings were combined. The solvents were removed in vacuo to leave an orange oil which was purified by reduced pressure flash chromatography over silica using a 9:1 mixture of ether and methanol as eluant.

Appropriate fractions were combined and the solvents removed in vacuo to leave an oil (1.2 g) which was dissolved in ether. The solution was saturated with hydrogen chloride to give a solid which was collected by filtration and dried in vacua to give a white solid (1 g), m.p. 90°–150° C.

The solid was dissolved in ethanol, the solution was saturated with hydrogen chloride, and the solvent was removed in vacuo. The residue was dissolved in the minimum amount of hot 2-propanol and the solution allowed to cool to ambient temperature whereupon it deposited a mixture of a white solid and a gum. The mixture was gently heated and triturated until all of the brown gum had been converted into a white solid. The mixture was cooled and the solid collected by filtration, washed with ether, and dried in vacua to give N-(1,4-benzodioxan-2-ylmethyl)-1-[1-(quinazolin-4-yl)piperid-4-yl]methylamine dihydrochloride as a white solid (0.6 g), m.p. 210°–216° C.

EXAMPLE 5

A mixture of 2-chloropyridine (19.4 g), 1-(piperid-4-yl)methylamine (14.25 g), sodium carbonate (11.4 g) and 3-methyl-1-butanol (100 ml), was stirred and heated under reflux for 16 hours, then filtered. The solvent was removed in vacuo to leave an oil which was distilled to give 1-[1-(pyrid-2-yl)piperid-4-yl]methylamine as a pale yellow oil (5.65 g), b.p. 126°–130° C. at 0.6 mbar.

A mixture of the oil (3.4 g), 1,4-benzodioxan-2-ylmethyl toluene-4-sulphonate (5.7 g, prepared in a similar manner to that described in Example 1), potassium carbonate (4.5 g) and acetonitrile (45 ml) was stirred and heated under reflux for 48 hours then filtered. The solvent was removed in vacuo to leave an oil which was purified by reduced pressure flash chromatography over silica using a 9:1 mixture of ether and methanol as eluant. Appropriate fractions were combined and the solvents removed in vacuo to leave an oil. The oil was dissolved in ether and the solution saturated with hydrogen chloride to give a solid which was collected by filtration, washed with ether and dried in vacuo to give N-(1,4-benzodioxan-2-ylmethyl)-1-[1-(pyrid-2-yl)piperid-4-yl]methylamine dihydrochloride as a white solid (3.65 g), m.p. 217°–228° C.

EXAMPLE 6

A mixture of 8-hydroxy-1,4-benzodioxan-2-ylmethanol (10 g—prepared in a similar manner to that described in U.S. Pat. No. 3,101,354), sodium hydroxide (2.2 g) and water (150 ml) was stirred for 30 minutes, then cooled to 0° C. Methyl iodide (3.42 ml) was added dropwise, then the mixture was heated to 80° C. and stirred for 4 hours. The mixture was cooled to ambient temperature and stirred for 16 hours. The product was extracted into ethyl acetate (2×200 ml), and the combined extracts were washed with saturated sodium thiosulphate solution (2×200 ml), dried over magnesium sulphate, and the solvent removed in vacuo to yield 1-(8-methoxy-1,4-benzodioxan-2-yl)methanol as a solid (6.89 g)

A solution of toluene-4-sulphonyl chloride (5.84 g) in pyridine (10 ml) was added dropwise at 10°–15° C. to a solution of 1-(8-methoxy-1,4-benzodioxan-2-yl)methanol (5.0 g) in pyridine (30 ml) and the mixture was stirred at ambient temperature for 20 hours. The mixture was poured onto an excess of ice and dilute hydrochloric acid. The resulting solid was collected by filtration, washed with water and dried in vacuo to yield 8-methoxy-1,4-benzodioxan-2-ylmethyl toluene-4-sulphonate as a white solid (6.61 g), m.p. 66°–68° C.

1-(2-Methoxyphenyl)piperidine-4-carboxamide (12.53 g, prepared in a similar manner to that described in Example 2)

was added in portions to a stirred suspension of lithium aluminium hydride (4.36 g) in tetrahydrofuran (900 ml) under nitrogen. The resulting mixture was stirred at ambient temperature for 72 hours. Aqueous sodium hydroxide solution (5M; 5 ml) and water (5 ml) were added, and the resulting solid removed by filtration. The solvent was removed from the filtrate in vacuo, and the residue dissolved in ethyl acetate (500 ml). The organic layer was washed with water (2×300 ml), dried over magnesium sulphate and the solvent removed in vacuo to yield a brown oil (13 g). The oil was subjected to flash chromatography over silica, using a 1:1 mixture of ethyl acetate and methanol as eluant to remove impurities. The silica gel from the column was then suspended in methanol and the mixture was heated under reflux for 3 hours, filtered and the solvent removed in vacuo to yield 1-[1-(2-methoxyphenyl)piperid-4-yl]methylamine as a light brown oil (4.8 g).

A stirred mixture of 8-methoxy-1,4-benzodioxan-2-ylmethyl toluene-4-sulphonate (1.12 g), 1-[1-(2-methoxyphenyl)-piperid-4-yl]methylamine (0.7 g), potassium carbonate (1 g) and potassium iodide (catalytic amount) in acetonitrile (50 ml) was heated under reflux for 120 hours. The solvent was removed in vacuo and the residue was dissolved in ethyl acetate (100 ml). The solution was washed with water (50 ml) and the product was extracted into hydrochloric acid (5M, 3×70 ml). The acidic extracts were combined, washed with ether (50 ml), basified by the addition of aqueous sodium hydroxide solution (5M) and extracted into ethyl acetate (3×200 ml). The organic extracts were combined, dried over magnesium sulphate and the solvent removed in vacuo to yield a light brown oil (0.85 g). The oil was dissolved in ether (30 ml) and hydrogen chloride was bubbled through the solution. The resulting solid was collected by filtration and dried immediately in vacuo to yield N-(8-methoxy-1,4-benzodioxan-2-ylmethyl)-1-[1-(2-methoxyphenyl)piperid-4-yl]methylamine dihydrochloride as a white solid (0.24 g), m.p. 160° C. (dec).

EXAMPLE 7

A mixture of potassium carbonate (7.25 g) and dimethylformamide (200 ml) was irradiated with ultrasound until a cloudy, fine suspension was formed. Catechol (5.8 g) and (R)-glycidyl toluene-4-sulphonate (10 g) were added and the resulting mixture was stirred and heated at 60° C. for 36 hours. The mixture was allowed to cool then poured onto ice water (200 ml) and the product extracted into ether (3×300 ml). The combined extracts were washed with brine (3×200 ml), dried over magnesium sulphate and the solvent removed in vacuo to yield a white solid (7 g). The solid was crystallised from an ethyl acetate and petroleum ether (b.p. 40°–60° C.) mixture to yield (S)-1,4-benzodioxan-2-ylmethanol as a white crystalline solid (3.47 g).

Toluene-4-sulphonyl chloride (4.2 g) was added at –10° C. under nitrogen to a stirred solution of (S)-1,4-benzodioxan-2-ylmethanol (3.3 g) in pyridine (50 ml) The mixture was allowed to warm to ambient temperature and was stirred for a further 60 hours, then poured onto ice-water (200 ml). The product was extracted into ethyl acetate (3×200 ml) then the combined extracts were washed with dilute hydrochloric acid (100 ml), and water (100 ml), dried over magnesium sulphate, and the solvent removed in vacuo. The resulting orange oil (5.84 g), which solidified slowly on standing, was purified by crystallisation from an ether and petroleum ether (b.p. 40°–60° C.) mixture to yield two batches of a white crystalline solid (2.4 and 1.2 g). The 2.4 g batch was recrystallised 3 times from ethanol, the solid obtained becoming each time less rich in the desired (R)-isomer of the product and was therefore discarded. The mother liquors from these 3 recrystallisations now contained predominantly the desired (R)-isomer of the product so they were combined, the solvent removed in vacuo and the residue recrystallised from ethanol to yield white crystals of (R)-1,4-benzodioxan-2-ylmethyl toluene-4-sulphonate (1.2 g); m.p. 105°–107° C.

A stirred mixture of 1-[1-(2-methoxyphenyl)piperid-4-yl] methylamine (0.84 g, prepared in a similar manner to that described in Example 2), (R)-1,4-benzodioxan-2-ylmethyl toluene-4-sulphonate (1.2 g), potassium carbonate (1 g), and potassium iodide (catalytic amount) in acetonitrile (50 ml) was heated under reflux for 90 hours. The solvent was removed in vacuo and the residue diluted with ethyl acetate (100 ml). The product was extracted into hydrochloric acid (5M, 3×70 ml) and the extracts combined and basified by the addition of aqueous sodium hydroxide solution (5M). The product was extracted into ethyl acetate (3×150 ml), and the combined extracts were washed with water (2×100 ml), dried over magnesium sulphate and the solvent removed in vacuo. The residue was purified by flash chromatography over silica using ethyl acetate as the eluant. Appropriate fractions were combined and the solvent removed in vacuo to leave a yellow oil which crystallised on standing. The product was then recrystallised from ethyl acetate to yield (S)-(−)-N-(1,4-benzodioxan-2-ylmethyl)-1-[1-(2-methoxyphenyl)-piperid-4-yl]methylamine as light brown crystals (0.41 g), m.p. 78°–79° C., $[\mu]_D^{25}$ −27.0° (c=1.0, $CH_2Cl_2$)

EXAMPLE 8

1,4-Benzodioxan-2-ylmethyl toluene-4-sulphonate (8 g, prepared in a similar manner to that described in Example 1), was added in portions over 30 minutes at 100°–140° C. to a solution of N-[3-(trifluoromethyl)pyrid-2-yl] ethanediamine (4.9 g) in xylene (36 ml) and the mixture was stirred at 140° C. for 6 hours and allowed to stand at ambient temperature for 48 hours.

The mixture was poured into water (200 ml) and the product extracted into dichloromethane. The extracts were washed with water, dried over magnesium sulphate and the solvents removed in vacuo to leave a brown oil (7.4 g) which was purified by reduced pressure flash chromatography over silica using ethyl acetate as eluant. Appropriate fractions were combined and the solvent removed in vacuo to leave two fractions of brown oil (1.35 g; fraction 1, and 0.6 g; fraction 2).

Fraction 1 (1.35 g) was dissolved in ether and the solution saturated with hydrogen chloride to give a solid which was collected by filtration, suspended in 2-propanol, heated under reflux for 5 minutes, cooled, collected by filtration, washed with ethyl acetate, and dried in vacuo at 40° C. to give a cream solid (1.4 g), m.p. 220°–224° C.

Fraction 2 (0.6 g) was dissolved in ether and the solution was saturated with hydrogen chloride to give a solid which was collected by filtration and dried in vacuo at 45° C. to give a brown solid (0.7 g). The solid was suspended in ethyl acetate, heated under reflux for 5 minutes, cooled, collected by filtration, suspended in propan-2-ol, heated under reflux for 5 minutes, cooled, collected by filtration, washed with ethyl acetate and dried in vacuo at 45° C. to give a cream solid (0.55 g), m.p. 220°–224° C.

The two crops of solid were combined, ground to a powder, and dried in vacuo to give N-(1,4-benzodioxan-2-ylmethyl)-N'-[3-(trifluoro methyl)-2-pyridyl)]-ethanediamine dihydrochloride as a cream solid (1.75 g), m.p. 222°–224° C.

EXAMPLE 9

Dimethyl sulphate (120 ml) was added dropwise at 70° C. under nitrogen over 1 hour to a stirred mixture of 1,6-dihydroxynaphthalene (100 g), sodium hydroxide (75 g) and water (600 ml) and the mixture was stirred at 70° C. for a further 3 hours. More dimethyl sulphate (30 ml) was added and the mixture was stirred at ambient temperature for 16 hours, then diluted with water (1000 ml). The product was extracted into ether (3×500 ml) and the extracts were washed with water (3×500 ml), dried over magnesium sulphate and the solvent removed in vacua. The residue was distilled to give 1,6-dimethoxynaphthalene as an oil (95 g), b.p. 100°–130° C. at 0.6 mbar, which solidified on standing at ambient temperature.

n-Butyllithium (2.5M in hexanes; 220 ml) was added dropwise at 700° C. under nitrogen to a stirred solution of 1,6-dimethoxynaphthalene (95 g) in tetrahydrofuran (1000 ml). N,N,N',N'-Tetra-methylethylenediamine (150 ml) was added and the mixture was stirred at ambient temperature for 20 hours, then cooled to −20° C. and poured onto crushed solid carbon dioxide (500 g). When effervescence had ceased, the mixture was diluted with water (1000 ml), basified by the addition of sodium carbonate (100 g), washed with ether (2×100 ml) and acidified by the addition of concentrated hydrochloric acid. The product was extracted into ethyl acetate and the extracts were washed with brine, dried over magnesium sulphate, and the solvents removed in vacuo. The residue crystallised from ethyl acetate to give a solid which was collected by filtration, dried in vacuo, and ground to give 3,8-dimethoxy-2-naphthoic acid as a cream powder (45.6 g), m.p. 151°–153° C. Concentration of the liquor yielded a second crop of 3,8-dimethoxy-2-naphthoic acid (5.4 g).

Lithium (1.2 g; 27 cm of 3.2 mm diameter wire) was added in small pieces to a stirred mixture of 3,8-dimethoxy-2-naphthoic acid (5 g), tetrahydrofuran (45 ml), t-butanol (10 ml) and liquid ammonia (130 ml) until the blue colour persisted for 5 minutes. Ammonium chloride (10 g) was added, and the ammonia was allowed to evaporate. The residue was acidified by the addition of hydrochloric acid (5M) and the product was extracted into ethyl acetate. The extracts were washed with water, dried over magnesium sulphate and the solvents were removed in vacuo to leave a yellow solid which crystallised from aqueous methanol as lustrous buff plates of 8-methoxy-1,2,3,4-tetrahydronaphthalene-2-carboxylic acid (3.2 g), m.p. 136°–138° C.

The above procedure was repeated using 3,8-dimethoxy-2-naphthoic acid (46 g), tetrahydrofuran (400 ml), t-butanol (100 ml), liquid ammonia (1200 ml) and lithium wire (11 g; 250 cm of 3.2 mm diameter wire). The product was obtained as buff platelets (29.35 g).

A solution of 8-methoxy-1,2,3,4-tetrahydronaphthalene-2-carboxylic acid (5 g) in tetrahydrofuran (50 ml) was brought to reflux temperature under nitrogen and borane-dimethyl sulphide complex (10M solution in dimethyl sulphide; 5 ml) was added dropwise. The mixture was then heated under gentle reflux for 5 hours, allowed to stand at ambient temperature for 16 hours, then cooled in ice and quenched by the cautious addition of water. The mixture was then acidified by the addition of 5M hydrochloric acid, heated to drive off dimethyl sulphide, cooled, basified by the addition of aqueous sodium hydroxide solution (5M), and the product extracted into ethyl acetate. The extracts were washed with water, dried over magnesium sulphate, and the solvents were removed to leave 1-(8-methoxy-1,2,3,4-tetrahydronaphth-2-yl)methanol as a pale yellow syrup (3.8 g), which solidified slowly at ambient temperature.

A solution of toluene-4-sulphonyl chloride (1.3 g) in pyridine (1.4 ml) was added dropwise to a stirred solution of 1-(8-methoxy-1,2,3,4-tetrahydronaphth-2-yl)methanol (1.0 g) in pyridine (2.4 ml) and the mixture was stirred at ambient temperature for 64 hours and then at 35°–52° C. for 4 hours. The mixture was then poured into ice-water and the product extracted into dichloromethane. The extracts were washed with ice-cold hydrochloric acid (5M) and ice-cold water, then dried over magnesium sulphate. The solvents were removed in vacuo to leave an orange oil (1.15 g).

The above procedure was repeated by addition of a solution of toluene-4-sulphonyl chloride (2.75 g), in dry pyridine (3.0 ml) to a solution of the alcohol (2.2 g) in pyridine (5.15 ml). The mixture was stirred for 6 hours at 35°–50° C., allowed to stand overnight at ambient temperature and worked up as above to give an orange oil (2.8 g).

The orange oils were combined (3.95 g) and dissolved in pyridine (75 ml). A solution of toluene-4-sulphonyl chloride (4.1 g) in pyridine (4.5 ml) was added and the mixture was stirred at ambient temperature for 24 hours, then poured into ice-cold hydrochloric acid (5M). Petroleum ether (b.p. 40°–60° C.) was added and the mixture was triturated until solidification of the product was complete. The solid was collected by filtration, washed with water and petroleum ether (b.p. 40°–60° C.), and dried in vacuo at 45°–50° C. to give 8-methoxy-1,2,3,4-tetrahydronaphth-2-ylmethyl toluene-4-sulphonate as a solid (2.9 g), m.p. 53°–58° C.

Finely powdered 2-chloropyrimidine (15.4 g) was added in portions over 40 minutes to a hot (95° C.) stirred mixture of 1-(piperid-4-yl)methylamine (30 g), sodium carbonate (30 g) and 3-methyl-1-butanol (100 ml). The mixture was stirred at 95° C. for 18 hours, cooled, diluted with ethyl acetate, and filtered. The solvents were removed in vacuo to leave a dark brown oil which was distilled to give a pale yellow oil (12.2 g), b.p. 126°–130° C. at 1 mbar. The oil was dissolved in ether and the solution was saturated with hydrogen chloride. Ethanol was added and the mixture triturated to give a solid which was collected by filtration, washed with ether, and dried in vacuo at 40° C. to give 1-[1-(pyrimidin-2-yl)piperid-4-yl]methylamine dihydrochloride as a pale yellow solid (9.75 g), m.p. 240°–245° C.

The dihydrochloride salt of 1-[1-(pyrimidin-2-yl)piperid-4-yl]methylamine (2.2 g) was basified by addition to aqueous sodium hydroxide solution (5M) and the free base extracted into ethyl acetate (2×25 ml). The extracts were washed with water, dried over magnesium sulphate and the solvent removed in vacuo to give an orange oil (1.6 g). The oil was added in one portion to a mixture of 8-methoxy-1,2,3,4-tetra-hydronaphth-2-ylmethyl toluene-4-sulphonate (2.9 g), potassium carbonate (2.5 g) and acetonitrile (25 ml), and the mixture was stirred and heated under reflux for 30 hours under nitrogen. The mixture was allowed to cool, then it was filtered and the filter cake washed with acetonitrile. The filtrate and washings were combined and the solvent removed in vacuo to leave an orange oil (3.2 g).

The oil was purified by reduced pressure flash chromatography over silica using a 9:1 mixture of ether and methanol as eluant. Appropriate fractions were combined and the solvent removed in vacuo to leave a yellow oil (2.1 g).

The oil was dissolved in 2-propanol (20 ml) and concentrated hydrochloric acid (5 ml) was added. Removal of the solvents left a very hygroscopic solid. The solid was suspended in aqueous sodium hydroxide solution (5M) and the product extracted into ethyl acetate. The extracts were dried over magnesium sulphate and added to a solution of fumaric acid (0.7 g) in methanol (10 ml). The resulting solution was diluted with ethyl acetate, and concentrated under reduced pressure until a white solid precipitated. The solid was collected by filtration and crystallised from a 4:1 mixture of ethyl acetate and industrial methylated spirit (50 ml) to give a white solid (1.1 g), m.p. 184°–186° C., which was found to be N-(8-methoxy-1,2,3,4-tetrahydronaphth-2-ylmethyl)-1-[1-(pyrimidin-2-yl)piperid-4-yl]methylamine 1.1 hydrochloride rather than the expected fumarate salt.

EXAMPLE 10

The recrystallisation liquors remaining after isolation of the product described in Example 9 were rebasified by the addition of aqueous sodium hydroxide solution (5M) and the free base extracted into ethyl acetate. The extracts were washed with water, dried over magnesium sulphate, filtered and the solvents removed in vacuo to give N-(8-methoxy-1,2,3,4-tetrahydronaphth-2-ylmethyl)-1-[1-(pyrimidin-2-yl) piperid-4-yl]methylamine as a brown oil (0.35 g). The oil was dissolved in dichloromethane (14 ml) and boron tribromide (1M solution in dichloromethane; 3.5 ml) was added under nitrogen. The mixture was stirred under nitrogen at ambient temperature for 24 hours then methanol (5 ml) was added. The mixture was stirred at ambient temperature for 10 minutes, then the solvent was removed by distillation at atmospheric pressure to leave a green oil which was triturated with hot 2-propanol to give a pale brown solid (0.5 g), m.p. 85°–90° C.

An attempted crystallisation from a 1:2 mixture of industrial methylated spirit and ethyl acetate gave a gum. Decantation of the supernatant liquor and trituration of the residue with acetone gave a solid which was collected by filtration and dried in vacuo to give 7-{N-[1-(pyrimidin-2-yl)piperid-4-ylmethyl}-aminomethyl)-5,6,7,8-tetrahydronaphth-1-ol dihydrobromide as a pale brown solid (0.14 g), m.p. >110° C. (dec).

EXAMPLE 11

A mixture of 3-methoxyphenol (50 g), ethyl vinyl ether (60 ml), dichloromethane (250 ml) and trichloroacetic acid (1.3 g) was stirred at ambient temperature for 20 hours, diluted with ether (1000 ml), washed with aqueous sodium hydroxide solution (0.5M, 2×100 ml) and brine (100 ml), dried over potassium carbonate and the solvent removed in vacuo. The residual 3-(1-ethoxyethoxy)anisole was used without purification.

The 3-(1-ethoxyethoxy)anisole was dissolved in ether (750 ml) and n-butyllithium (1.6M solution in hexanes; 500 ml) was added dropwise at ambient temperature under nitrogen. The mixture was stirred at ambient temperature for 2 hours, then it was cooled to 10° C. and a solution of dimethylformamide (94 g) in ether (150 ml) was added dropwise. The mixture was stirred at ambient temperature for 2 hours, then poured onto crushed ice. The product was extracted into ether, the combined extracts dried over magnesium sulphate, and the solvents removed in vacuo. The residual oil was dissolved in methanol (500 ml) and the stirred solution was cooled in ice and made strongly acidic by the addition of hydrochloric acid (2M). The resulting solid was collected by filtration, washed with water, dried in vacuo over phosphorus pentoxide and crystallised from petroleum ether (b.p. 60°–80° C.) to give 2-hydroxy-6-methoxybenzaldehyde as pale yellow needles (16 g), m.p. 69°–71° C.

The whole procedure was repeated, starting from 3-methoxyphenol (111.2 g). In the second step of the procedure, the reaction mixture was stirred at ambient temperature for 16 hours prior to addition to crushed ice. The product was obtained as two crops of pale yellow needles after crystallisation from petroleum ether (b.p. 40°–60° C.). The two crops were combined and recrystallised from petroleum ether (b.p. 40°–60° C.) to give 2-hydroxy-6-methoxybenzaldehyde as pale yellow needles (40 g).

A mixture of 2-hydroxy-6-methoxybenzaldehyde (29.2 g), 1,4-diazabicyclo[2.2.2]octane (DABCO) (7.5 g) and ethyl acrylate (100 ml) was heated at 95° C. for 16 hours. The mixture was diluted with ethyl acetate (500 ml), cooled to ambient temperature, washed with saturated aqueous sodium hydrogen carbonate solution (2×100 ml), hydrochloric acid (5M; 2×100 ml) and water (2×100 ml), dried over magnesium sulphate, and the solvent removed in vacuo to leave a brown oil.

The oil was dissolved in ethanol (500 ml) and potassium hydroxide (30 g) and water (500 ml) were added. The mixture was heated under reflux for 3 hours and allowed to stand at ambient temperature for 16 hours. The mixture was diluted with water, washed with ether (2×200 ml) and acidified to pH 1 by the addition of concentrated hydrochloric acid. A solid precipitated and was collected by filtration, washed with water, and triturated with ether to give a pale brown solid (4.3 g). The ether liquor was allowed to concentrate at ambient temperature for 16 hours to give further pale brown solid (0.9 g). The combined solid was 5-methoxy-2H-1-benzopyran-3-carboxylic acid (5.2 g), m.p. 209°–211° C.

A mixture of 5-methoxy-2H-1-benzopyran-3-carboxylic acid (12.25 g, prepared in a similar manner to that described above), 10% palladium-on-carbon catalyst (3 g) and ethanol (250 ml) was hydrogenated at 1 atmosphere for 1 hour. Hydrogen uptake was slow, so further catalyst (3 g) was added, and hydrogenation continued for 5 hours. The mixture was filtered and the solvent removed in vacuo to leave a semisolid which crystallised from 2-propanol to give a mass of pale yellow crystals which was broken up, collected by filtration, washed with ice-cold 2-propanol, dried in vacuo, ground to a powder, and redried in vacuo to give 5-methoxy-3,4-dihydro-2H-1-benzopyran-3-carboxylic acid as a buff powder (7.4 g), m.p. 147°–150° C.

Borane-dimethyl sulphide complex (10M solution in dimethyl sulphide; 1 ml) was added at ambient temperature under nitrogen to a stirred solution of 5-methoxy-3,4-dihydro-2H-1-benzopyran-3-carboxylic acid (1.0 g) in tetrahydrofuran (10 ml) and the mixture was heated under reflux for 5 hours and allowed to stand at ambient temperature under nitrogen for 16 hours.

The mixture was cooled in ice and quenched by the dropwise addition of water until effervescence ceased, then the mixture was acidified by the addition of hydrochloric acid (5M) and heated at approximately 95° C. to removed dimethyl sulphide. The mixture was then cooled in ice and basified by the addition of aqueous sodium hydroxide solution (5M). The product was extracted into ethyl acetate and the extracts were washed with saturated brine then dried over magnesium sulphate. The solvents were removed in vacuo to leave 1-(5-methoxy-3,4-dihydro-2H-1-benzopyran-3-yl)methanol as a pale yellow oil (1 g)

The reaction was repeated as above using the remaining 5-methoxy-3,4-dihydro-2H-1-benzopyran-3-carboxylic acid (6.0 g), in tetrahydrofuran (60 ml) and borane-dimethyl sulphide complex (6 ml). This gave further 1-(5-methoxy-3,4-dihydro-2H-1-benzopyran-3-yl)methanol (5.6 g).

A solution of toluene-4-sulphonyl chloride (8.1 g) in pyridine (9 ml) was added dropwise at ambient temperature to a solution of 1-(5-methoxy-3,4-dihydro-2H-1-benzopyran-3-yl)methanol (6.5 g) in pyridine (15.2 ml), then the mixture was stirred at ambient temperature for 3 hours and allowed to stand for 16 hours at ambient temperature. Further toluene-4-sulphonyl chloride (2.0 g) was added and the mixture was stirred at ambient temperature for 6 hours and allowed to stand at ambient temperature for 72 hours. The mixture was poured into an excess of hydrochloric acid (5M) and ice, and the product was extracted into ethyl acetate. The extracts were washed with ice-cold water, then dried over magnesium sulphate and the solvent was removed in vacuo to leave a yellow oil (6.6 g). The oil (6.6 g) was dissolved in dichloromethane (50 ml) and 4-(dimethylamine)pyridine (DMAP) (3.35 g) was added. The solution was then cooled to 0° C. and toluene-4-sulphonyl chloride (4.8 g) was added in one portion. The mixture was stirred at 0° C. while the toluene-4-sulphonyl chloride dissolved then the cooling bath was removed and the solution was stirred at ambient temperature for 16 hours. The mixture was concentrated in vacuo to 20 ml and diluted with ethyl acetate to precipitate a white solid. The mixture was filtered and the filtrate diluted with more ethyl acetate to give a second crop of solid, and re-filtered. The filtrate from crop 2 was allowed to stand at ambient temperature for 72 hours to give a third precipitate of solid, and re-filtered. The solvents were removed in vacuo to leave 5-methoxy-3,4-dihydro-2H-1-benzopyran-3-ylmethyl toluene-4-sulphonate as a yellow oil (7.0 g) which was used without further purification.

A mixture of 5-methoxy-3,4-dihydro-2H-1-benzopyran-3-ylmethyl toluene-4-sulphonate (7.0 g), potassium carbonate (5.6 g) and acetonitrile (57 ml) was stirred at 60° C. and 1-[1-(pyrimidin-2-yl)piperid-4-yl]methylamine (3.1 g, prepared in similar manner to that described in Example 9) was added. The mixture was stirred and heated under reflux under nitrogen for 24 hours, allowed to cool and filtered. The filter pad was washed with acetonitrile, and the filtrate and washings combined. The solvent was removed in vacuo to leave an orange oil (7.5 g) which was purified by reduced pressure flash chromatography over silica using a 9:1 mixture of ether and methanol as eluant. Appropriate fractions were combined and the solvents removed in vacuo to leave two fractions of oil (3.6 g—slightly impure; 1.5 g—pure product).

The pure oil (1.5 g) was dissolved in ethyl acetate (40 ml) and added to a solution of fumaric acid (0.45 g) in industrial methylated spirit (20 ml). The resulting solution was diluted to 100 ml with ethyl acetate and cooled to 0° C. The resulting precipitate was collected by filtration, washed with ethyl acetate and dried in vacuo to give N-(5-methoxy-3,4-dihydro-2H-1-benzopyran-3-ylmethyl)-1-(1-(pyrimidin-2-yl)piperid-4-yl]methylamine monofumarate as a white solid (1.5 g), m.p. 202°–204° C.

EXAMPLE 12

A mixture of 4-carbamoyl-1-(2,4-dinitrophenyl) pyridinium chloride (50 g, prepared in a similar manner to that described in Example 2), aniline (35 ml) and methanol (11) was stirred at ambient temperature for 48 hours. The resulting suspension was heated at 50° C. for 1 hour, then cooled and the solvent removed in vacuo. The solid residue was triturated with acetone (2×11) then collected by filtration to give 4-carbamoyl-1-phenylpyridinium chloride (33.24 g), mp 290°–292° C.

A mixture of 4-carbamoyl-1-phenylpyridinium chloride (13 g), 10% palladium-on-carbon catalyst (260 mg) and ethanol (250 ml) was hydrogenated at ambient temperature and pressure for 2 days. The solution was filtered (Celite) and the filtrate was concentrated to approximately 50 ml. This solution was cooled and the solid precipitate collected by filtration to give 1-phenylpiperidine-4-carboxamide (5.99 g).

The Celite pad was washed thoroughly with hot ethanol and the solvent was removed in vacuo. The residue was combined with the filtrate from above and the mixture was heated under reflux for 0.5 hour. The solid which precipitated on cooling was collected by filtration to give further 1-phenylpiperidine-4-carboxamide (3.42 g). Total yield 9.41 g.

1-Phenylpiperidine-4-carboxamide (1.5 g) was added portionwise to a stirring suspension of lithium aluminium hydride (0.5 g) in dry tetrahydrofuran (100 ml) under nitrogen. The resulting suspension was stirred at ambient termperature for 2 hours, then heated under reflux for 2 hours. The mixture was cooled, and water (0.5 ml), then concentrated sodium hydroxide solution (0.5 ml) were added. The resulting precipitate was removed by filtration (Celite). The filtrate was dried over magnesium sulphate, and the solvent removed in vacuo to yield 1-(1-phenylpiperid-4-yl)methylamine (1.15 g).

The above process was repeated on a 4.33× scale to yield 1-(1-phenylpiperid-4-yl)methylamine (5.1 g).

A stirred mixture of 1-(1-phenylpiperid-4-yl) methylamine (6 g), 1,4-benzodioxan-2-ylmethyl toluene-4-sulphonate (10.1 g, prepared in a similar manner to that described in Example 1), potassium carbonate (15 g) and acetonitrile was heated under reflux for 72 hours. The resulting mixture was cooled and filtered. The solvent was removed in vacuo, and the residue dissolved in ethyl acetate. This solution was filtered through a silica pad using ethyl acetate (500 ml) as eluant, then the solvent was removed in vacuo. The residue was dissolved in ether and hydrogen chloride was bubbled through the solution. The resulting solid was collected by filtration, triturated with a 25:1 mixture of ethyl acetate and methanol (250 ml), then refiltered to yield N-(1,4-benzodioxan-2-ylmethyl)-1-(1-phenylpiperid-4-yl)methylamine dihydrochloride as a white solid (5.64 g), m.p. 278°–280° C.

EXAMPLE 13

A mixture of 1,4-benzodioxan-5-ylamine (3.5 g, prepared in a similar manner to that described in Zh.Org.Khim.1967, 3,1121), 4-carbamoyl-1-(2,4-dinitrophenyl)pyridinium chloride (6.8 g, prepared in a similar manner to that described in Example 2) and methanol (150 ml) was stirred at ambient temperature for 16 hours. Methanol (100 ml) was added and the resulting mixture was heated under reflux for 3 hours then allowed to stand at ambient temperature for 2.5 days. Further 1,4-benzodioxan-5-ylamine (0.35 g) was added and the mixture was heated under reflux for 24 hours. The solvent was removed in vacuo and the residue was triturated with ether. The resulting solid was crystallised from a 1:1 mixture of 2-propanol and ethyl acetate to give a pale yellow solid. The solvents were removed from the filtrate in vacuo and the residue was triturated with acetone to give further yellow solid. This was combined with the solid obtained from the crystallisation to give crop (1) (3.57 g).

A mixture of 1,4-benzodioxan-5-ylamine (3.0 g), 4-carbamoyl-1-(2,4-dinitrophenyl)pyridinium chloride (5.8 g) and methanol (150 ml) was stirred and heated under reflux for 16 hours. The solvent was removed in vacuo and the residue triturated with ether. The ether was removed by decantation, and the solid residue was triturated with hot acetone. The resulting mixture was cooled and filtered to give crop (2) of a yellow solid (5.30 g).

Crops (1) and (2) were combined and triturated with hot acetone. The mixture was cooled and the resulting solid collected by filtration and dried in vacuo to give 1-(1,4-benzodioxan-5-yl)-4-carbamoylpyridinium chloride as a yellow solid (8.7 g), m.p. 256°–258° C.

1-(1,4-Benzodioxan-5-yl)-4-carbamoylpyridinium chloride (2.0 g) was added to 10% palladium-on-carbon catalyst (1.8 g) under nitrogen. Ammonium formate (3.5 g) was added and the resulting mixture was stirred while methanol (35 ml) was added dropwise. The resulting mixture was heated under reflux for 3.5 hours. Ammonium formate which crystallised in the condenser was washed back in with methanol (35 ml). The mixture was cooled and filtered (Celite) under nitrogen. The filtrate was basified by the addition of solid sodium hydrogen carbonate and the solvent removed in vacuo. The residue was diluted with water (100 ml) and the product extracted into dichloromethane (3×100 ml). The combined extracts were washed with water (100 ml), dried over magnesium sulphate, filtered and the solvent removed in vacuo to give 1-(1,4-benzodioxan-5-yl) piperidine-4-carboxamide as a white solid (1.27 g), m.p. ~194° C.

A mixture of 1-(1,4-benzodioxan-5-yl)piperidine-4-carboxamide (4.1 g, prepared in a similar manner to that described above) and tetrahydrofuran (400 ml) was added dropwise to a stirred mixture of lithium aluminium hydride (1.2 g) in tetrahydrofuran (100 ml) under nitrogen. The resulting mixture was stirred at ambient temperature for 2 hours. Further lithium aluminium hydride (0.4 g) was added and the resulting mixture was stirred for a further 1.5 hours.

Water (3 ml) and concentrated sodium hydroxide solution (3 ml) were added, and the mixture was stirred for 15 minutes, then filtered (Celite). The Celite pad was washed with ethyl acetate. The filtrates were combined and the solvents removed in vacuo. The residue was dissolved in dichloromethane, and the solution was dried over magnesium sulphate, filtered and the solvent removed in vacuo to give 1-[1-(1,4-benzodioxan-5-yl)piperid-4-yl]methylamine as an orange oil (4.19 g) which was used without further purification.

A mixture of the orange oil (4.19 g), 1,4-benzodioxan-2-ylmethyl toluene-4-sulphonate (5.0 g, prepared in a similar manner to that described in Example 1), potassium carbonate (4.32 g) and acetonitrile (100 ml) was stirred under reflux for 30 hours and then allowed to stand at ambient temperature for 2.5 days. The resulting mixture was filtered and the solvent removed in vacuo to give an orange oil (8.0 g).

The oil was purified by flash chromatography over silica using, sequentially, a 1:1 then a 1:2 mixture of petroleum ether (b.p. 40°–60° C.) and ethyl acetate, then ethyl acetate and then methanol as eluants. The solvents were removed from the appropriate fractions in vacua and the residue (2.7 g), was dissolved in a mixture of ethyl acetate and methanol. The solution was saturated with hydrogen chloride, the solvents were removed in vacua and the residue crystallised from a mixture of methanol and ethyl acetate to give N-(1,4-benzodioxan-2-ylmethyl)-1-[1-(1,4-benzodioxan-5-yl)piperid-4-yl]methylamine dihydrochloride as a light pink solid (2.6 g), m.p. 226°–228° C.

EXAMPLE 14

A stirred mixture of 1-[1-(2-methoxyphenyl)piperid-4-yl] methylamine (0.89 g, prepared in a similar manner to that described in Example 2), (S)-1,4-benzodioxan-2-ylmethyl toluene-4-sulphonate (1.3 g), potassium carbonate (1 g) and a few crystals of potassium iodide in acetonitrile (50 ml) was heated under reflux for 72 hours. The solvent was removed in vacua, water (50 ml) was added and the product extracted into ethyl acetate (3×50 ml). The combined organic extracts were dried over magnesium sulphate and the solvent removed in vacua. The product was purified by flash chromatography over silica using ethyl acetate as eluant. Appropriate fractions were combined and the solvent removed in vacuo to yield a white crystalline solid (0.69 g). The solid was recrystallised 6 times from ethanol, to yield (R)-(+)-N-(1,4-benzodioxan-2-ylmethyl)-1-[1-(2-methoxyphenyl) piperid-4-yl]methylamine (0.4 g), m.p. 79°–82° C., $[\alpha]_D^{26}$= +25.6° (c=1.0; $CH_2Cl_2$)

EXAMPLE 15

A mixture of 2-(chloromethyl)-1,4-benzodioxan (20.0 g) and ethyl piperidine-4-carboxylate (34.04 g) was stirred and heated at 130° C. for 3.5 hours. On cooling, the mixture partially solidified. Water (100 ml) was added and the product was extracted into ethyl acetate (3×100 ml). The combined extracts were dried over magnesium sulphate, filtered and the solvent removed in vacua to yield a brown oil (35 g). The oil was purified by Kügelrohr distillation; the fraction remaining after heating at 250° C./5.3 mbar was ethyl 1-(1,4-benzodioxan-2-ylmethyl)piperidine-4-carboxylate (31.5 g).

A solution of ethyl 1-(1,4-benzodioxan-2-ylmethyl) piperidine-4-carboxylate (5 g) in industrial methylated spirit (100 ml) was added to a solution of potassium hydroxide (4 g) in water (50 ml). The mixture was stirred at ambient temperature for one hour then heated under reflux for 6 hours. The solution was cooled and the solvent removed in vacua. The residue was diluted with water then neutralised by the addition of dilute hydrochloric acid. The product was extracted into ethyl acetate and the extract was dried over magnesium sulphate. The solvent was removed in vacuo to give crude 1-(1,4-benzodioxan-2-ylmethyl)piperidine-4-carboxylic acid (0.28 g). The aqueous phase was then evaporated to dryness and the residue triturated with a 25:1 mixture of dichloromethane and methanol (2×100 ml). The inorganic residues were removed by filtration and the solvent was removed from the filtrate in vacuo to give a further crop of the crude desired product (5.03 g) which was used without further purification.

Ethyl chloroformate (0.1 g) was added dropwise to a stirred solution of 1-(1,4-benzodioxan-2-ylmethyl) piperidine-4-carboxylic acid (0.28 g) and triethylamine (0.12 g) in chloroform (10 ml) at 0° C. After 30 minutes a solution of 2-methoxyaniline (0.12 g) in chloroform (5 ml) was added and the mixture stirred at ambient temperature for 16 hours. The reaction mixture was then washed sequentially with water, aqueous sodium hydroxide solution (1M), hydrochloric acid (1M) and water. The solution was dried over magnesium sulphate, the solvent was removed in vacuo, and the residue was eluted through a silica column using a 1:1 mixture of petroleum ether (b.p. 40°–60° C.) and ethyl acetate as eluant. The solvent was removed in vacuo to yield 1-(1,4-benzodioxan-2-ylmethyl)-N-(2-methoxyphenyl)piperidine-4-carboxamide as a solid (50 mg). This procedure was repeated on 9X scale with the following changes. The reaction was heated to 50° C. for 1 hour after being stirred at ambient temperature for 16 hours. The solvent was then removed in vacuo and the residue was eluted through a silica column as previously described. Further desired product (1.05 g) was obtained.

Borane-dimethyl sulphide complex (1M solution in dimethyl sulphide; 0.5 ml) was added dropwise under nitrogen to a solution of 1-(1,4-benzodioxan-2-ylmethyl)-N-(2-methoxyphenyl)piperidine-4-carboxamide (0.35 g) in dry tetrahydrofuran (25 ml) and then the mixture was heated under reflux for 2 hours. The reaction was cooled and the solvents removed in vacuo. The residue was diluted cautiously with dilute hydrochloric acid (1M; 70 ml) and heated at 95° C. for 1.5 hours. The aqueous mixture was cooled and basified by the addition of aqueous sodium hydroxide solution (2.5M), there the product was extracted into dichloromethane. The organic extract was washed with water, then dried over magnesium sulphate, filtered, and the solvent removed in vacuo to yield 1-[1-(1,4-benzodioxan-2-ylmethyl)piperid-4-yl]-N-(2-methoxyphenyl) methylamine (0.32 g). The procedure was repeated using 1-(1,4-benzodioxan-2-ylmethyl)-N-(2-methoxyphenyl)piperidine-4-carboxamide (1.37 g, prepared in a similar manner to that described above). The products of the two reactions were combined and dissolved in ether. Hydrogen chloride was bubbled through the solution and the resulting solid precipitate collected by filtration (1.2 g). The solid was dissolved in saturated aqueous sodium hydrogen carbonate solution (100 ml) and the resulting oil extracted into ethyl acetate (100 ml). An excess of a saturated solution of oxalic acid in ethyl acetate was added and the solid precipitate was collected by filtration and dried in vacuo at 50° C. to yield 1-[1-(1,4-benzodioxan-2-ylmethyl) piperid-4-yl]-N-(2-methoxyphenyl)methylamine mono-oxalate (0.78 g), m.p. 215°–218° C.

EXAMPLE 16

A mixture of 4-carbamoyl-1-(2,4-dinitrophenyl)-pyridinium chloride (50 g, prepared in a similar manner to that described in Example 2), 4-methoxyaniline (40 g) and methanol (1800 ml) was stirred at ambient temperature for 16 hours. The solvent was removed in vacua and the residue was triturated with hot ether (1200 ml). The suspension was cooled, then filtered to give a golden solid (67.2 g). The solid was recrystallised from industrial methylated spirit (1500 ml) to give dark yellow crystals (45.6 g). Ether was added to the industrial methylated spirit and the resulting solid was collected by filtration to yield 4-carbamoyl-1-(4-methoxyphenyl)pyridinium chloride (3 g). The crystals (45.6 g) were suspended in acetone (500 ml), and the mixture was heated under reflux for a few minutes, then filtered. The resulting solid was extracted with acetone in a Soxhlet apparatus for 16 hours to remove unreacted starting material. The solid remaining was dried in vacua to yield further 4-carbamoyl-1-(4-methoxyphenyl)pyridinium chloride (31.8 g). Total yield 34.8 g.

A suspension of 4-carbamoyl-1-(4-methoxyphenyl)-pyridinium chloride (22.0 g) in methanol (250 ml) was hydrogenated at ambient temperature and pressure in the presence of 10% palladium-on-carbon catalyst (1.0 g) for 2 days. Further catalyst (0.75 g) was added, and when no more hydrogen was taken up, the catalyst was removed by filtration. The filtrate was basified by the addition of an excess of triethylamine and the solvent removed in vacua. The residue was partitioned between water and a 19:1 mixture of chloroform and methanol. The solvent was removed in vacuo from the organic layer and the residue dried in vacuo over phosphorus pentoxide to give 1-(4-methoxyphenyl) piperidine-4-carboxamide as a white solid (10 g), m.p. 178°–181° C.

Borane-dimethyl sulphide complex (15 ml; 10M in dimethyl sulphide) was added dropwise at 15°–20° C., under nitrogen, to a stirred suspension of 1-(4-methoxyphenyl) piperidine-4-carboxamide (10 g) in tetrahydrofuran (95 ml). The mixture was heated under reflux for 4 hours then allowed to stand at ambient temperature for 16 hours. Ice water was added to destroy excess reducing agent then the mixture was acidified by the addition of hydrochloric acid (5M) and washed with ether (200 ml). The aqueous layer was basified by the addition of concentrated aqueous sodium hydroxide solution then the product was extracted into ether (3×250 ml). The combined extracts were dried over magnesium sulphate and the solvent removed in vacuo. The residue was purified by flash chromatography over silica using a 9:1 mixture of dichloromethane and industrial methylated spirit as eluant. The solvents were removed in vacuo from the appropriate fractions to give 1-[1-(4-methoxyphenyl)-piperid-4-yl]methylamine as an oil (0.5 g).

A stirred mixture of 2-chloromethyl-1,4-benzodioxan (0.42 g), 1-[1-(4-methoxyphenyl)piperid-4-yl]methylamine (0.5 g) and potassium carbonate (1.0 g) in acetonitrile (50 ml) was heated under reflux for 7 hours. Triethylamine (0.32 ml) was added and stirring under reflux continued for 6 hours. 1,4-benzodioxan-2-ylmethyl toluene-4-sulphonate (0.73 g, prepared in a similar manner to that described in Example 1) was added, and the mixture stirred under reflux for 7 hours. The solvent was removed in vacuo to give a yellow oil which was purified by flash chromatography over silica using dichloromethane then a 19:1 mixture of dichloromethane and industrial methylated spirit as eluant. The fractions containing the desired product were collected and the solvents removed in vacuo to give a golden oil (0.20 g). The oil was dissolved in ether (50 ml) and hydrogen chloride was bubbled through the solution. The resulting white solid was collected by filtration, washed with ether and dried immediately in vacuo to yield N-(1,4-benzodioxan-2-ylmethyl)-1-[1-(4-methoxyphenyl) piperid-4-yl] methylamine dihydrochloride (0.13 g), m.p. 268°–270° C.

EXAMPLE 17

A stirred mixture of N-(3-bromopropyl)phthalimide (26.8 g), 2-methoxyaniline (24.6 g) and xylene (60 ml) was heated for 4 hours at 140° C. After cooling, the solvent was removed in vacuo. A mixture of the resulting oil, industrial methylated spirit (100 ml) and hydrazine hydrate (6.9 g) was heated under reflux with stirring for 1 hour. The mixture was cooled and acidified by the addition of hydrochloric acid (5M). The white precipitate was removed by filtration and the solvent removed from the filtrate in vacuo. The residue was dissolved in water (15 ml) and basified by the addition of aqueous sodium hydroxide solution (5M). The resulting oil was extracted into dichloromethane (2×50 ml). The extracts were dried and the solvent removed in vacuo to give a mobile red oil (16.5 g). The oil was purified by flash chromatography over silica using dichloromethane, then a 9:1 mixture of dichloromethane and industrial methylated spirit, then methanol as eluant. The desired fractions were collected and the solvents removed in vacuo to give N-(2-methoxyphenyl)-1,3-propanediamine as a golden mobile oil (8.5 g).

A stirred mixture of 8-methoxy-1,4-benzodioxan-2-ylmethyl toluene-4-sulphonate (2.4 g, prepared in a similar manner to that described in Example 6), N-(2-methoxyphenyl)-1,3-propanediamine (1.30 g), potassium iodide (catalytic amount) and potassium carbonate (1.8 g) in acetonitrile (120 ml) was heated under reflux for 24 hours. After cooling the mixture was filtered and the solvent removed from the filtrate in vacuo to give a reddish oil (3.57 g). The oil was purified by flash chromatography over silica using a 19:1 mixture of dichloromethane and industrial methylated spirit as eluant. The desired fractions were collected and the solvent removed in vacuo to give a yellow oil (1.4 g). The oil was dissolved in ether (50 ml) and hydrogen chloride was bubbled through the solution to give a white hygroscopic solid. The oily solid was collected by filtration and partitioned between dilute aqueous sodium hydroxide solution and dichloromethane. The organic layer was separated, dried over magnesium sulphate and the solvent removed in vacuo to give a yellow oil. The oil was dissolved in ether (50 ml) and an excess of a saturated solution of maleic acid in ether was added dropwise. The resulting white solid was collected by filtration and dried in vacuo to give N-(8-methoxy-1,4-benzodioxan-2-ylmethyl)-N'-(2-methoxyphenyl)-1,3-propanediamine maleate as a solid (0.35 g), m.p. 59°–62° C.

EXAMPLE 18

A mixture of 4-carbamoyl-1-(2,4-dinitrophenyl)-pyridinium chloride (43.2 g, prepared in a similar manner to that described in Example 2), 3-methoxyaniline (34 g) and methanol (1500 ml) was stirred at ambient temperature for 16 hours. The mixture was then warmed at 40° C. for 30 minutes, and stirring was continued for 2 hours at ambient temperature, then the solvent was removed in vacuo. Ether was added to the resulting oily solid and the solid collected by filtration. The solid was triturated in hot 2-propanol (1l), collected by filtration and dried. The solid was triturated in hot acetone, collected by filtration and dried to give 4-carbamoyl-1-(3-methoxyphenyl)pyridinium chloride as a beige solid (32.4 g), m.p. 272° C. (dec).

A suspension of 4-carbamoyl-1-(3-methoxyphenyl)-pyridinium chloride (26 g) in methanol (300 ml) was hydrogenated at ambient temperature and pressure in the presence of 10% palladium-on-carbon catalyst (2.0 g) until hydrogen uptake ceased (~2 days) The mixture was filtered, excess triethylamine added and the solvent removed in vacuo to give a pink solid. This was partitioned between water and chloroform. The organic phase was dried and the solvent removed in vacuo to give 1-(3-methoxyphenyl)piperidine-4-carboxamide as a pink solid (19 g), m.p. 153°–156° C.

Borane-dimethyl sulphide complex (1M in dimethyl sulphide; 12.2 ml) was added dropwise at 15°–20° C. under nitrogen to a stirred suspension of 1-(3-methoxyphenyl) piperidine-4-carboxamide (8.0 g) in tetrahydrofuran (75 ml). The suspension gradually dissolved. When the addition was complete, the mixture was heated under reflux for 4 hours, then allowed to stand at ambient temperature for 16 hours. The reaction was then quenched by dropwise addition to stirred ice/water. The aqueous mixture was acidified by the addition of dilute hydrochloric acid and washed with ether (200 ml). The insoluble material present was removed by filtration and discarded. The aqueous layer was basified by the addition of concentrated aqueous sodium hydroxide solution then cooled and the product extracted into ether (3×250 ml). The combined extracts were dried over magnesium sulphate and the solvent removed in vacuo to give an opaque oil (4.7 g). The oil was purified by flash chromatography over silica using a 9:1 mixture of dichloromethane and industrial methylated spirit then methanol as eluant. The desired fractions were collected and the solvent removed in vacuo to give 1-[1-(3-methoxyphenyl)piperid-4-yl] methylamine as a golden oil (2.9 g).

A stirred mixture of 1,4-benzodioxan-2-ylmethyl toluene-4-sulphonate (4.2 g, prepared in a similar manner to that described in Example 1), 1-[1-(3-methoxyphenyl) piperid-4-yl]methylamine (2.9 g) and potassium carbonate (4 g) in acetonitrile (250 ml) was heated under reflux for 3 days. The potassium carbonate was removed by filtration and washed with acetonitrile. The solvent was removed from the filtrate in vacuo to give a cloudy oil (6.0 g). The oil was purified by flash chromatography over silica using a 19:1 mixture of dichloromethane and industrial methylated spirit as eluant. The desired fractions were collected and the solvents removed in vacuo to give a yellow oil (2.3 g). The oil was dissolved in ether and hydrogen chloride was bubbled through the stirred solution. The resulting white solid was collected by filtration, washed with ether and dried in vacuo to give N-(1,4-benzodioxan-2-ylmethyl)-1-[1-(3-methoxyphenyl) piperid-4-yl]methylamine hydrochloride as a solid (0.93 g), m.p. 186°–188° C.

EXAMPLE 19

Racemic N-(1,4-benzodioxan-2-ylmethyl)-1-[1-(pyrid-2-yl) piperid-4-yl]methylamine (1.5 g, prepared by basification of the dihydrochloride salt obtained in a similar manner to that described in Example 5) was resolved into its separate enantiomers by preparative high performance liquid chromatography on a chiralcel (type OC) column of internal dimensions 25 cm×2 cm, with a 1:1 mixture of isohexane and ethanol as eluant. Appropriate fractions were combined, and the solvents were removed in vacuo.

The first eluted fraction was dissolved in ether, the solution was saturated with hydrogen chloride and the resulting solid was collected by filtration and dried in vacuo to give (−)-N-(1,4-benzodioxan-2-ylmethyl)-1-[1-(pyrid-2-yl) piperid-4-yl]methylamine dihydrochloride as a white solid (0.5 g), m.p. 228°–232° C., $[\alpha]_D^n = -63.0°$ (c=1; methanol).

EXAMPLE 20

The second eluted fraction obtained from the preparative high performance liquid chromatography resolution described in Example 19 was dissolved in ether, the solution was saturated with hydrogen chloride and the resulting solid was collected by filtration and dried in vacuo to give (+)-N-(1,4-benzodioxan-2-ylmethyl)-1-[1-pyrid-2-yl) piperid-4-yl]methylamine dihydrochloride as a white solid (0.55 g), m.p. 227°–230° C., $[\alpha]_D^n = +63.0°$ (c=1; methanol).

EXAMPLE 21

A solution of 1-(6,7-dichloro-1,4-benzodioxan-2-yl) methanol (12.88 g, prepared in a similar manner to that described in Gazz. Chim. Ital 1965,95,1447), in pyridine (9 ml) was added dropwise to an ice cooled, stirred solution of toluene-4-sulphonyl chloride (12 g) in pyridine (21 ml). The mixture was allowed to warm to ambient temperature and was stirred for 60 hours. The mixture was poured onto water (150 ml), acidified by the addition of concentrated hydrochloric acid and the product extracted into ethyl acetate (4×80 ml). The combined extracts were washed with water (2×100 ml) and brine, then dried over magnesium sulphate and the solvent removed in vacuo to give an orange oil (17.5 g) which slowly solidified. The solid was triturated with ether (2×100 ml), collected by filtration and recrystallised from acetonitrile to give 6,7-dichloro-1,4-benzodioxan-2-ylmethyl toluene-4-sulphonate (6.6 g), as white crystals, m.p. 124°–125° C.

A mixture of 6,7-dichloro-1,4-benzodioxan-2-ylmethyl toluene-4-sulphonate (3 g), 1-[1-(2-methoxyphenyl) piperid-4-yl]methylamine (1.65 g, prepared in a similar manner to that described in Example 2), potassium carbonate (2.1 g) and dimethylformamide (25 ml) was stirred at 85°

C. under nitrogen for 16 hours, then poured onto water (150 ml). The product was extracted into ethyl acetate (4×80 ml), the combined extracts were washed with water (2×100 ml) and brine, then dried over magnesium sulphate and the solvent removed in vacuo, to give an off-white gum. This was purified by flash chromatography over silica using a 1:20 mixture of methanol and dichloromethane as eluant. Appropriate fractions were combined and the solvents removed in vacuo to give a solid (0.54 g). The solid was dissolved in ether, an excess of ethereal hydrogen chloride solution was added, then the solvent was removed in vacuo. The residue was dried by azeotropic distillation with 2-propanol, then triturated with hot ethanol, and the solid collected by filtration and dried in vacuo to yield N-(6,7-dichloro-1,4-benzodioxan-2-ylmethyl)-1-[1-(2-methoxyphenyl) piperid-4-yl]methylaminehydrochloride (280 mg), m.p. 248°–252° C. (dec).

EXAMPLE 22

A mixture of 4-carbamoyl-1-(2,4-dinitrophenyl)-pyridinium chloride (41 g) and 2-chloroaniline (20 g) in methanol (500 ml) was stirred at ambient temperature for 24 hours. The mixture was then heated under reflux for 24 hours and then a further portion of 2-chloroaniline (10 g) was added. Heating under reflux was continued for a further 48 hours then another portion of 2-chloroaniline (10 g) was added. The mixture was heated for a further 48 hours, then cooled and the solvent removed in vacuo. The residue was triturated with hot acetone (2×11), cooled and the solid collected by filtration. The solid was dissolved in hot methanol (100 ml), treated with charcoal and hot filtered. Hot ethyl acetate (500 ml) was added to the filtrate and the solution was allowed to cool. The resulting solid was collected by filtration, washed with ethyl acetate and dried to give crude 4-carbamoyl-1-(2-chlorophenyl)-pyridinium chloride (23.69 g) which was used without further purification.

The crude product from the previous reaction (2.5 g) in ethanol was hydrogenated at ambient temperature and pressure for 7 hours in the presence of 10% rhodium-on-carbon catalyst (0.25 g). More catalyst was added (0.5 g) and hydrogenation continued for 8 hours. A further portion (0.5 g) of catalyst was added and hydrogenation continued for 6 hours. The catalyst was removed by filtration (Celite) and the filtrate was basified by the addition of saturated aqueous sodium hydrogen carbonate solution. The solvent was removed in vacuo and the solid residue crystallised from ethyl acetate, removing insoluble inorganic material by filtration, to give 1-(2-chlorophenyl)piperidine-4-carboxamide (0.5 g).

1-(2-chlorophenyl)piperidine-4-carboxamide (0.25 g, prepared in a similar manner to that described above) was dissolved in tetrahydrofuran (25 ml) and borane-dimethyl sulphide complex (1M in dimethyl sulphide; 0.4 ml) was added. The resulting solution was heated under reflux for 2 hours. The solvent was removed in vacuo, hydrochloric acid (1M; 50 ml) was added, and the mixture stirred at ambient temperature for 1 hour. The solution was basified by the addition of aqueous sodium hydroxide solution (5M) and the product extracted into ether. The extracts were washed with water then dried over magnesium sulphate and the solvent removed in vacuo to give 1-[1-(2-chlorophenyl)piperid-4-yl]methylamine as an oil (0.19 g). The reaction was repeated on a 4.4× scale to give further 1-[1-(2-chlorophenyl)piperid-4-yl]methylamine (1.0 g).

A mixture of 1,4-benzodioxan-2-ylmethyl toluene-4-sulphonate (1.68 g, prepared in a similar manner to that described in Example 1), 1-[1-(2-chlorophenyl)piperid-4-yl] methylamine (1.8 g) and potassium carbonate (10 g) in acetonitrile (150 ml) was heated under reflux with stirring for 24 hours. Potassium iodide (0.2 g) was added to the reaction mixture and heating under reflux continued for a further 24 hours. The cooled mixture was filtered and the solvent removed from the filtrate in vacuo. The residue was passed through a silica column using a 1:1 mixture of petroleum ether (b.p. 40°–60° C.) and ethyl acetate as eluant. The solvent was removed from the eluate in vacuo and the clear oily residue dissolved in ether. An excess of an etheral solution of hydrogen chloride was added, and the solvent removed in vacuo to give N-(1,4-benzodioxan-2-ylmethyl)-1-[1-(2-chlorophenyl)piperid-4-yl]methylamine hydrochloride (0.37 g), m.p. 275°–278° C. (dec).

EXAMPLE 23

Epichlorohydrin (18.3 ml) was added dropwise under nitrogen to a solution of 3-fluorocatechol (10 g) and potassium hydroxide (4.56 g) in water (45 ml) and the mixture heated under reflux for 4½ hours. The mixture was cooled and the product extracted into ethyl acetate (3×50 ml). The organic extract was washed with aqueous sodium hydroxide solution (25%), then brine, then dried over magnesium sulphate. The solvent was removed in vacuo to give a crude mixture of 1-(5-fluoro-1,4-benzodioxan-2-yl)methanol and 1-(8-fluoro-1,4-benzodioxan-2-yl)methanol (15.5 g).

A solution of the crude mixture of isomers from the previous reaction (15.5 g) and toluene-4-sulphonyl chloride (14.88 g) in pyridine (20 ml) was stirred at ambient temperature for 18 hours. Water (100 ml) was added and the products extracted into ethyl acetate (3×50 ml). The organic extract was washed with dilute hydrochloric acid, then brine, and dried over magnesium sulphate. The solvent was removed in vacuo and the residue purified by flash chromatography over silica using a 1:1 mixture of cyclohexane and ether as eluant. Appropriate fractions were combined and the residue obtained after removal of the solvent in vacuo was further purified by flash chromatography on silica using a 7:3 mixture of cyclohexane and ether as eluant. The solvent was removed from the appropriate fractions in vacuo to give a mixture of 5-fluoro-1,4-benzodioxan-2-ylmethyl toluene-4-sulphonate and 8-fluoro-1,4-benzodioxan-2-ylmethyl toluene-4-sulphonate (4.5 g).

A stirred mixture of the isomeric products from the previous reaction (4.5 g), 1-[1-(2-methoxyphenyl)-piperid-4-yl]methylamine (2.93 g), potassium carbonate (3.68 g) and acetonitrile (100 ml) was heated under reflux for 18 hours. The cooled solution was passed through a pad of silica using a 2:1 mixture of ethyl acetate and petroleum ether (b.p. 40°–60° C.) as eluant to remove residual starting toluene-4-sulphonate ester, then neat ethyl acetate to elute the required product. The solvent was removed in vacuo, the residue dissolved in ether and an excess of an ethereal solution of hydrogen chloride was added. The resulting precipitate was collected by filtration and dried in vacuo to give a mixture of N-(5-fluoro-1,4-benzodioxan-2-ylmethyl)-1-[1-(2-methoxyphenyl) piperid-4-yl]methylamine hydrochloride and N-(8-fluoro-1,4-benzodioxan-2-ylmethyl)-1-[1-(2-methoxyphenyl) piperid-4-yl]methylamine hydrochloride (260 mg) m.p. 228°–30° C.

EXAMPLE 24

Epichlorohydrin (2.32 g) was added dropwise to a stirred solution of 1,2-dihydroxynaphthalene (4.0 g) and potassium hydroxide (4.0 g) in water (32 ml) and the resulting mixture stirred at 60°–80° C. for 2.5 hours then poured into water (100 ml). The product was extracted into ether (6×100 ml), a small volume of methanol being added to aid solubility. The combined extracts were washed with aqueous sodium hydroxide solution (1M), then water, and dried over magnesium sulphate. The solvent was removed in vacuo to give crude 1-(naphtho[1,2-b]dioxan-2-yl)methanol (4.0 g) as a dark oil which was used without further purification.

A solution of the crude product from the previous reaction (4.0 g) and toluene-4-sulphonyl chloride (3.53 g) in pyridine (10 ml) was stirred at ambient temperature for 3 hours then further toluene-4-sulphonyl chloride (200 mg) was added and the mixture allowed to stand for 18 hours. The mixture was poured into water (100 ml) and the product was extracted into ethyl acetate (3×100 ml). The combined extracts were washed with hydrochloric acid (5M; 2×100 ml), saturated aqueous sodium hydrogen carbonate solution (2×100 ml) and brine, then dried over magnesium sulphate. The solvent was removed in vacuo to leave a red oil which was purified by flash chromatography over silica using a 85:15 mixture of cyclohexane and ether as eluant. The solvent was removed in vacuo from the fractions containing the required product and the residue crystallised from a mixture of ether and ethyl acetate to afford nearly pure naphtho [1, 2-b]dioxan-2-ylmethyl toluene-4-sulphonate (0.48 g) as a pink solid.

The reaction was repeated on 4.15× scale affording further product (1.75 g). The final products from the two reactions were combined and recrystallised from ethyl acetate to give pure naphtho[1, 2-b]dioxan-2-ylmethyl toluene-4-sulphonate as a white solid (1.38 g) m.p. 122°–124° C.

A mixture of the product from the previous reaction (1.32 g), 1-[1-(2-methoxyphenyl)piperid-4-yl]methylamine (0.79 g), potassium carbonate (1.0 g) -and acetonitrile (50 ml) was stirred and heated under reflux for 40 hours. The cooled mixture was filtered, the solvent removed in vacuo and the residue purified by flash chromatography over silica using ethyl acetate as eluant. The solvent was removed from the appropriate fraction in vacuo and the resulting white solid dissolved in ethyl acetate. The solution was saturated with hydrogen chloride, and the resulting solid collected by filtration and dried in vacuo to give 1-[1-(2-methoxyphenyl) piperid-4-yl]-N-(naphtho[1, 2-b]dioxan-2-ylmethyl) methylamine hydrochloride 1.3 hydrate (0.86 g), m.p. 182°–185° C.

EXAMPLE 25

A mixture of 2,3-dihydrobenzo[b]furan-7-ylamine (6.8 g prepared in a similar manner to that described in Tetrahedron Letters 1982,23,147), 4-carbamoyl-1-(2,4-dinitrophenyl) pyridinium chloride (14.7 g prepared in a similar manner to that described in Example 2) and methanol (400 ml) was stirred under reflux for 5 hours then allowed to stand at ambient temperature and heated for 16 hours. The solvent was removed in vacuo, and the residue was triturated with hot acetone, cooled and filtered to give 1-(2,3-dihydrobenzo [b]furan-7-yl)-4-carbamoylpyridinium chloride as a yellow solid (11.5 g), m.p. 289°–290° C.

1-(2,3-dihydrobenzo([b]furan-7-yl)-4-carbamoylpyridinium chloride (12.7 g, prepared in a similar manner to that described above) was added to 10% palladium-on-carbon catalyst (12.3 g) under nitrogen. Ammonium formate (23.5 g) was added and the resulting mixture was stirred while methanol (250 ml) was added dropwise. The mixture was heated under reflux for 4 hours (ammonium formate which crystallised in the condenser was washed back into the mixture with methanol (~150 ml)). After cooling, the mixture was filtered (Celite) under nitrogen (being careful not to let the catalyst dry out), basified by the addition of saturated sodium hydrogen carbonate solution, the solvent removed in vacuo, and the residue diluted with water. The product was extracted into dichloromethane (3×100 ml). The combined organic extracts were washed with water, dried over magnesium sulphate, filtered and the solvent removed in vacua to give a pink solid (7.57 g). This was triturated with hot ethyl acetate, cooled and filtered to give crude 1-[2,3-dihydrobenzo[b]furan-7-yl] piperidine-4-carboxamide as a light pink solid (6.64 6), which was used without further purification.

A solution of the light pink solid (6.6 g) in tetrahydrofuran (500 ml) was added dropwise under nitrogen to a stirred mixture of lithium aluminium hydride (2.05 g) in tetrahydrofuran (250 ml). The resulting mixture was stirred at ambient temperature for 16 hours, then water (4 ml) and concentrated aqueous sodium hydroxide solution (4 ml) were added. The resulting mixture was stirred for 30 minutes and then filtered (Celite). The solvent was removed in vacua and the residue was dissolved in dichloromethane. The solution was dried over magnesium sulphate, filtered and the solvent removed in vacua to give 1-[1-(2,3-dihydrobenzo [b]furan-7-yl)piperid-4-yl]methylamine as an orange oil (6.24 g), which was used without further purification.

A mixture of 8-methoxy-1,4-benzodioxan-2-ylmethyl toluene-4-sulphonate (2.12 g, prepared in a similar manner to that described in Example 6), 1-[1-(2,3-dihydrobenzo[b] furan-7-yl) piperid-4-yl]methylamine (1.4 g), potassium carbonate (1.67 g) and acetonitrile (50 ml) was stirred under reflux for 4 days. The mixture was poured onto water (50 ml) and the product extracted into ethyl acetate (3×50 ml). The extracts were washed with brine (50 ml), dried over magnesium sulphate, filtered, and the solvent removed in vacua to give a gum. The gum was purified by flash chromatography over silica using a 2:1, then a 1:1 mixture of ethyl acetate and petroleum ether (b.p. 60°–80° C.) as eluant. The solvent was removed from the appropriate fraction in vacuo and the residue was dissolved in ether. An excess of ethereal hydrogen chloride solution was added, then the solvent was removed in vacuo to give 1-[1-(2,3-dihydrobenzo[b]furan-7-yl) piperid-4-yl]-N-(8-methoxy-1, 4-benzodioxan-2-ylmethyl) methylamine hydrochloride as a solid (180 mg), m.p. 194°–196° C.

EXAMPLE 26

A mixture of 4-chlorocatechol (5.0 g) in 10% aqueous potassium hydroxide solution (20 ml) was stirred under nitrogen, epichlorohydrin (9.6 g) was added, and the mixture heated at 95° C. for 4 hours. The mixture was cooled to ambient temperature and the product extracted into ether (2×50 ml). The extracts were washed with aqueous sodium hydroxide solution (5M; 50 ml) and water (50 ml), dried over magnesium sulphate, filtered and the solvent removed in vacuo to give a yellow oil (8.24 g). The oil was purified by flash chromatography over silica using a 10:1, then 4:1, then 1:1 mixture of petroleum ether (b.p. 40°–60° C.) and ethyl acetate, then ethyl acetate, as eluant. Appropriate fractions were combined and the solvents removed in vacuo to give a cream solid (6.0 g).

A mixture of the solid (6.0 g), pyridine (40 ml) and toluene-4-sulphonyl chloride (17.1 g) was stirred at ambient temperature for 16 hours, then poured onto water (200 ml). The product was extracted into ethyl acetate (3×100 ml) then the extracts were washed with hydrochloric acid (5M, 2×100 ml), saturated aqueous sodium hydrogen carbonate solution (2×100 ml), then brine (100 ml). The extracts were dried over magnesium sulphate, filtered and the solvent removed in vacuo to give a yellow oil (11.39 g). The oil was purified by flash chromatography over silica using an 85:15 mixture of cyclohexane and ether as eluant. Appropriate fractions were combined and the solvents removed in vacuo to give 8 fractions. Each fraction was analysed by nuclear magnetic resonance spectroscopy.

Fraction 4 was recrystallised from ether to give a white solid (0.44 g) which was a 9:1 mixture of 7-chloro and 6-chloro-1,4-benzodioxan-2-ylmethyl toluene-4-sulphonate.

Fractions 5 and 6 were combined and purified further by flash chromatography over silica using an 85:15 mixture of cyclohexane and ether as eluant to yield 3 fractions (A, B and C).

Fraction A was recrystallised from ether to give a white solid (1.2 g), and combined with the recrystallised product of fraction 4 to give a total yield of 1.64 g of the 9:1 isomer mixture.

A stirred mixture of the combined solid, (1.5 g), 1-[1-(2-methoxyphenyl)piperid-4-yl]methylamine (0.93 g), potassium carbonate, (1.2 g) and acetonitrile (50 ml) was heated under reflux for 40 hours. The mixture was cooled, filtered and the solvent removed in vacuo. The residual oil was purified by flash chromatography over silica using ethyl acetate as eluant. The resulting oil was dissolved in ether and hydrogen chloride bubbled through to give a colourless solid which was collected by filtration, washed with ethyl acetate and dried to give an approximately 9:1 mixture of N-(7-chloro-1,4-benzodioxan-2-ylmethyl)-1-[1-(2-methoxyphenyl) piperid-4-yl]methylamine and N-(6-chloro-1,4-benzodioxan-2-ylmethyl)-1-[1-(2-methoxyphenyl) piperid-4-yl]methylamine hydrochloride hydrate (0.87 g) m.p. 237°–240° C.

EXAMPLE 27

Fraction 7 from the first column chromatography purification described in the second stage of Example 26 was recrystallised from ether to give a white solid (0.21 g). This was combined with fraction C from the column chromatography purification described in Example 26 to give a total yield of 1.40 g of a 4:6 mixture of 7-chloro and 6-chloro-1,4-benzodioxan-2-ylmethyl toluene-4-sulphonate.

A stirred mixture of the approximate 4:6 mixture of p-toluenesulphonate esters from the previous reaction (1.3 g), 1-[1-(2-methoxyphenyl)piperid-4-yl]methylamine (1.5 g), potassium carbonate (1.01 g) and acetonitrile (80 ml) was heated under reflux for 30 hours. The cooled mixture was filtered then the solvent removed in vacuo to give an oil which was purified by flash chromatography over silica using ethyl acetate as eluant. The solvent was removed from the appropriate fractions in vacuo and the resulting oil dissolved in ether. The solution was saturated with hydrogen chloride and the resulting solid collected by filtration and dried in vacuo to give an approximately 4:6 mixture of N-(7-chloro-1,4-benzodioxan-2-ylmethyl)-1-[1-(2-methoxyphenyl) piperid-4-yl]methylamine and N-(6-chloro-1,4-benzodioxan-2-ylmethyl)-1-[1-(2-methoxy phenyl)-piperid-4-yl]methylamine 1.7 hydrochloride hydrate (0.69 g) m.p. 237°–240 ° C.

EXAMPLE 28

Toluene-4-sulphonyl chloride (10 g) was added in portions at −10° C. to a stirred solution of 1-(8-hydroxy-1,4-benzodioxan-2-yl) methanol (4.9 g) in dry pyridine (50 ml) under nitrogen. The solution was stirred for 4 hours, allowed to stand at ambient temperature for 48 hours then poured into ice-water (100 ml). The water was decanted from the resulting gum which was then dissolved in dichloromethane (200 ml). The solution was washed with water (2×200 ml), dried over magnesium sulphate and the solvent removed in vacuo to give a brown oil which crystallised on standing. Trituration with a 1:1 mixture of ethanol and methanol gave crude [8-(toluene-4-sulphonato)-1,4-benzodioxan-2-yl] methyl toluene-4-sulphonate as an off-white solid (1.6 g), which was used without further purification.

A mixture of the crude product from the previous reaction (1.6 g), 1-[1-(2-methoxyphenyl)piperid-4-yl]methylamine (0.72 g), potassium carbonate (1.0 g) and potassium iodide (catalytic amount) in acetonitrile (50 ml) was heated under reflux for 72 hours. The solvent was removed in vacuo and the residue dissolved in ethyl acetate (100 ml). The solution was washed with water then the product extracted into hydrochloric acid (5M; 3×70 ml). The combined extracts were washed with ethyl acetate (2×30 ml), basified with aqueous sodium hydroxide solution (5M), and the product extracted into ethyl acetate (3×150 ml). The extracts were combined, dried over magnesium sulphate and the solvent removed in vacuo to give a yellow oil which was purified by flash chromatography over silica using ethyl acetate as eluant. The appropriate fractions were combined and the solvent removed in vacuo. The residual oil was dissolved in ether (20 ml) and hydrogen chloride bubbled through to give an off-white solid which was collected by filtration then dried immediately in vacuo to afford [2-({[1-(2-methoxyphenyl) piperid-4-yl]methylamino}methyl)-1,4-benzodioxan-8-yl]toluene-4-sulphonate dihydrochloride (0.15 g), m.p. 225° C.

A solution of potassium hydroxide (1. 0 g) in water (19.7 ml) and ethanol (19.7 ml) was added in portions (~10 ml) at 15 minute intervals to [2-({[1-(2-methoxyphenyl)piperid-4-yl]methylamino}methyl)-1,4-benzodioxan-8-yl]toluene-4-sulphonate dihydrochloride (0.15 g). The mixture was heated under reflux for 2½ hours, cooled and neutralised with glacial acetic acid. The product was extracted into ether (3×100 ml) and the combined extracts allowed to stand for 16 hours. The precipitate which had then formed was collected by filtration and dried to give N-(8-hydroxy-1,4-benzodioxan-2-ylmethyl) -1-[1-(2-methoxyphenyl) piperid-4-yl]methylamine as a colourless solid (0.2 g), m.p. 116°–119° C.

EXAMPLE 29

The use of compounds of the present invention in the manufacture of pharmaceutical compositions is illustrated by the following description. In this description the term "active compound" denotes any compound of the invention but particularly any compound which is the final product of one of the preceding Examples.

a) Capsules

In the preparation of capsules, 10 parts by weight of active compound and 240 parts by weight of lactose are de-aggregated and blended. The mixture is filled into hard gelatin capsules, each capsule containing a unit dose of part of a unit dose of active compound.

b) Tablets
Tablets are prepared from the following ingredients.

|  | Parts by weight |
| --- | --- |
| Active compound | 10 |
| Lactose | 190 |
| Maize starch | 22 |
| Polyvinylpyrrolidone | 10 |
| Magnesium stearate | 3 |

The active compound, the lactose and some of the starch are de-aggregated, blended and the resulting mixture is granulated with a solution of the polyvinyl-pyrrolidone in ethanol. The dry granulate is blended with the magnesium stearate and the rest of the starch. The mixture is then compressed in a tabletting machine to give tablets each containing a unit dose or a part of a unit dose of active compound.

Enteric Coated Tablets

Tablets are prepared by the method described in (b) above. The tablets are enteric coated in a conventional manner using a solution of 20% cellulose acetate phthalate and 3% diethyl phthalate in ethanol:dichloromethane (1:1).

d) Suppositories

In the preparation of suppositories, 100 parts by weight of active compound is incorporated in 1300 parts by weight of triglyceride suppository base and the mixture formed into suppositories each containing a therapeutically effective amount of active ingredient.

We claim:

1. Compounds of formula I

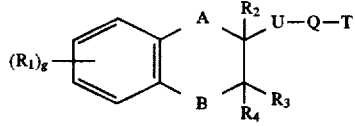

and pharmaceutically acceptable salts thereof in the form of individual enantiomers, racemates, or other mixtures of enantiomers, in which A is —O—;
B is —O—;
g is 0 or 1;
$R_1$ represents halo, an alkyl group having 1 to 3 carbon atoms, an alkoxy group having 1 to 3 carbon atoms, or hydroxy;
$R_2$, $R_3$ and $R_4$ are each H;
U is methylene;
Q is a group of formula IIa or IIc

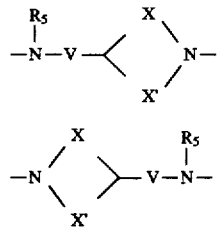

in which V is methylene or ethylene, X is an alkylene chain having 0 to 2 carbon atoms and X' is an alkylene chain having 1 to 4 carbon atoms provided that the total number of carbon atoms in X and X' amounts to 3 or 4; and $R_5$ is H; and T is pyridyl, pyrazinyl, phenyl, benzo[b]furanyl, 1–4, benzodioxanyl, or quinazolinyl all optionally substituted by methoxy, trifluoromethyl, or halo.

2. Compounds of formula I as defined in claim 1 wherein $R_1$ represents methoxy, fluoro, chloro or hydroxy.

3. Compounds of formula I as defined in claim 1 wherein T is 2-pyridyl, 2-pyrazinyl, phenyl, 2,3-dihydrobenzo(b)furan-7-yl, 1,4-benzodioxan-5-yl or 4-quinazolinyl all optionally substituted by methoxy, trifluoromethyl, or halo.

4. Compounds of formula I as defined in claim 1 selected from:

N-(1,4-Benzodioxan-2-ylmethyl)1-[1-(pyrazin-2-yl)piperid-4-yl]methylamine;
N-(1,4-Benzodioxan-2-ylmethyl)1-[1-(2-methoxyphenyl)piperid-4-yl]methylamine;
N-(1,4-Benzodioxan-2-ylmethyl)-1-[1-(3-chloropyrid-2-yl)piperid-4-yl]methylamine;
N-(1,4-Benzodioxan-2-ylmethyl)1-[1-(quinazolin-4-yl)piperid-4-yl]methylamine;
N-(1,4-Benzodioxan-2-ylmethyl)1-[1-(pyrid-2-yl)piperid-4-yl]methylamine;
N-(8-Methoxy-1,4-benzodioxan-2-ylmethyl)1-[1-(2-methoxyphenyl)piperid-4-yl]methylamine;
N-(1,4-Benzodioxan-2-ylmethyl)1-(1-phenylpiperid-4-yl)methylamine;
N-(1,4-Benzodioxan-2-ylmethyl)-1-[1-(1,4-benzodioxan-5-yl)piperid-4-yl]methylamine;
1-[1-(1,4-Benzodioxan-2-ylmethyl)piperid-4-yl]-N-(2-methoxyphenyl)methylamine;
N-(1,4-Benzodioxan-2-ylmethyl)-1-[1-(4-methoxyphenyl)piperid-4-yl]methylamine;
N-(1,4-Benzodioxan-2-yimethyl)-1-[1-(3-methoxyphenyl)piperid-4-yl]methylamine;
N-(1,4-Benzodioxan-2-ylmethyl)-1-[1-(2-chlorophenyl)piperid-4-yl]methylamine;
N-(5-Fluoro-1,4-benzodioxan-2-ylmethyl)1-[1-(2-methoxyphenyl)piperid-4-yl]methylamine;
N-(8-Fluoro-1,4-benzodioxan-2-ylmethyl)1-[1-(2-methoxyphenyl)piperid-4-yl]methylamine;
N-1-[1-(2,3-Dihydrobenzo[b]furan-7-yl)piperid-4-yl]-N-(8-methoxy-1,4-benzodioxan-2-ylmethyl)methylamine;
N-(6-Chloro-1,4-benzodioxan-2-ylmethyl)1-[1-(2-methoxyphenyl)piperid-4-yl]methylamine;
N-(7-Chloro-1,4-benzodioxan-2-ylmethyl)-1-[1-(2-methoxyphenyl)piperid-4-yl]methylamine;
N-(8-hydroxy-1,4-benzodioxan-2-ylmethyl)-1-[1-(2-methoxyphenyl)piperid-4-yl]methylamine;
and pharmaceutically acceptable salts thereof in the form of individual enantiomers, racemates, or other mixtures of enantiomers.

5. Compounds of formula I as defined in claim 4 which are:

(S)-(−)-N-(1,4-Benzodioxan-2-ylmethyl)-1-[1-(2-methoxyphenyl)piperid-4-yl]methylamine;
(R)-(+)-N-(1,4-Benzodioxan-2-ylmethyl)-1-[1-(2-methoxyphenyl)piperid-4-yl]methylamine;
(−)-N-(1,4-Benzodioxan-2-ylmethyl)-1-[1-(pyrid-2-yl)piperid-4-yl]methylamine dihydrochloride;
(+)-N-(1,4-Benzodioxan-2-ylmethyl)-1-[1-(pyrid-2-yl)piperid-4-yl]methylamine dihydrochloride.

6. The compound of formula I as defined in claim 4 which is:

N-(7-Chloro-1,4-benzodioxan-2-ylmethyl)-1-(1-(2-methoxyphenyl)piperid-4-yl)methylamine; and pharmaceutically acceptable salts thereof in the form of individual enantiomers, racemates, or other mixtures of enantiomers.

7. Pharmaceutical compositions comprising a therapeutically effective amount of a compound of formula I, as defined in claim 1, together with a pharmaceutically acceptable diluent or carrier.

8. A method of treating psychoses, which comprises the administration of a therapeutically effective amount of a compound of formula I as defined in claim 1 to a patient in need thereof.

9. A method as defined in claim 8 for treating schizophrenia.

10. A process for the preparation of compounds of formula I as defined in claim 1 comprising:

a) the reaction of a compound of formula III

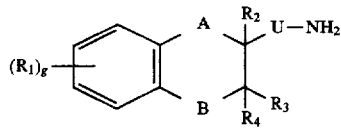

with a compound of formula IV

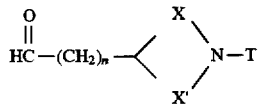

followed by reaction of the intermediate imine with a reducing agent to give compounds of formula I in which Q is a group of formula IIa in which $R_5$ is H and V is $(CH_2)_{n+1}$ wherein n=0 or 1;

b) the reaction of compound of formula III with a compound of formula V

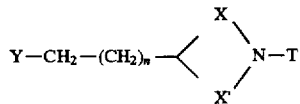

in which Y is a leaving group to give compounds of formula I in which Q is a group of formula IIa in which $R_5$ is H and V is $(CH_2)_{n+1}$ wherein n=0 or 1;

c) the reaction of compound of formula VI

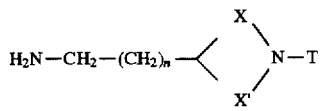

with a compound of formula VII

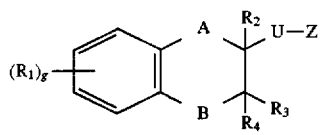

in which Z is a leaving group to give compounds of formula I in which Q is a group of formula IIa in which $R_5$ is H and U is $(CH_2)_{n+1}$ wherein n=0;

d) the reaction of compounds of formula VI with compounds of formula VIII

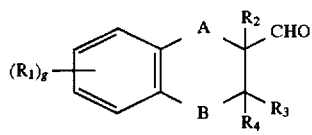

followed by reduction of the intermediate imine to give compounds of formula I in which U is methylene, Q is a group of formula IIa in which $R_5$ is H and V is $(CH_2)_{n+1}$ wherein n=0 or 1; or e) the reaction of a compound of formula XLII

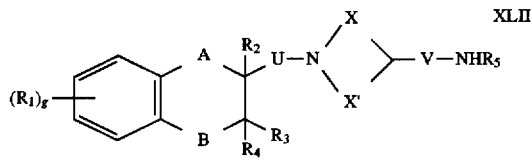

with a haloaromatic compound to give compounds of formula I in which Q is a group of formula IIc.

* * * * *

UNITED STATES PATENT AND TRADEMARK OFFICE
CERTIFICATE OF CORRECTION

PATENT NO.: 5,767,116

DATED: June 16, 1998

INVENTOR(S): KERRIGAN et al.

It is certified that error appears in the above-identified patent and that said Letters Patent is hereby corrected as shown below:

Col. 44, claim 4, line 32, "yimethyl" should be --ylmethyl--.

Signed and Sealed this

Twenty-ninth Day of September, 1998

Attest:

BRUCE LEHMAN

*Attesting Officer*     *Commissioner of Patents and Trademarks*